(12) United States Patent
Tran et al.

(10) Patent No.: US 8,481,731 B2
(45) Date of Patent: Jul. 9, 2013

(54) COMPOUNDS, PHARMACEUTICAL COMPOSITION AND METHODS RELATING THERETO

(75) Inventors: Joe A. Tran, San Marcos, CA (US); Chen Chen, San Diego, CA (US)

(73) Assignees: Boehringer Ingelheim International GmbH, Ingelheim am Rhein (DE); Neurocrine Biosciences, Inc., San Diego, CA (US)

(*) Notice: Subject to any disclaimer, the term of this patent is extended or adjusted under 35 U.S.C. 154(b) by 114 days.

(21) Appl. No.: 12/821,219

(22) Filed: Jun. 23, 2010

(65) Prior Publication Data

US 2011/0021491 A1 Jan. 27, 2011

Related U.S. Application Data

(60) Provisional application No. 61/220,125, filed on Jun. 24, 2009.

(51) Int. Cl.
| | | |
|---|---|---|
| C07D 401/14 | (2006.01) | |
| C07D 403/14 | (2006.01) | |
| C07D 487/04 | (2006.01) | |
| A61K 31/4427 | (2006.01) | |
| A61K 31/506 | (2006.01) | |
| A61P 3/04 | (2006.01) | |
| A61P 3/10 | (2006.01) | |

(52) U.S. Cl.
USPC ........... 544/309; 544/316; 544/320; 514/269; 514/275

(58) Field of Classification Search
USPC ................. 544/309, 316, 320; 514/269, 275
See application file for complete search history.

(56) References Cited

U.S. PATENT DOCUMENTS

| | | | |
|---|---|---|---|
| 6,221,660 B1 | 4/2001 | Bonini et al. | |
| 6,468,756 B1 | 10/2002 | Bonini et al. | |
| 7,083,933 B1 | 8/2006 | Griffin | |
| 7,108,991 B2 | 9/2006 | Chen et al. | |
| 7,135,471 B2 | 11/2006 | Eggenweiler et al. | |
| 2007/0078150 A1 | 4/2007 | Jones et al. | |
| 2009/0258816 A1 | 10/2009 | Fyee et al. | |
| 2009/0286812 A1 | 11/2009 | Erickson et al. | |
| 2010/0113479 A1 | 5/2010 | Choudhury et al. | |
| 2010/0113480 A1 | 5/2010 | Reuman | |
| 2010/0113773 A1 | 5/2010 | Kimura et al. | |
| 2010/0285145 A1* | 11/2010 | Darout et al. | 424/520 |
| 2010/0292259 A1* | 11/2010 | Kaneko et al. | 514/269 |
| 2011/0021491 A1 | 1/2011 | Tran et al. | |
| 2011/0166116 A1 | 7/2011 | Dyck et al. | |
| 2012/0028962 A1* | 2/2012 | Rikimaru et al. | 514/217.06 |
| 2012/0052130 A1* | 3/2012 | Darout et al. | 424/520 |

FOREIGN PATENT DOCUMENTS

| | | |
|---|---|---|
| CA | 2710182 A1 | 4/2009 |
| CA | 2720049 A1 | 10/2009 |
| EP | 1997484 A2 | 12/2008 |
| WO | 9952868 A1 | 10/1999 |
| WO | 02102783 A1 | 12/2002 |
| WO | 03104205 A1 | 12/2003 |
| WO | 2004043925 A2 | 5/2004 |
| WO | 2004065380 A1 | 8/2004 |
| WO | 2005007647 A1 | 1/2005 |
| WO | 2005061489 A1 | 7/2005 |
| WO | 2005121121 A2 | 12/2005 |
| WO | 2006067531 A1 | 6/2006 |
| WO | 2006067532 A1 | 6/2006 |
| WO | 2006070208 A1 | 7/2006 |
| WO | 2006076231 A2 | 7/2006 |
| WO | 2006077364 A1 | 7/2006 |
| WO | 2006077365 A1 | 7/2006 |
| WO | 2006077367 A1 | 7/2006 |
| WO | 2006083491 A2 | 8/2006 |
| WO | 2007003960 A1 | 1/2007 |
| WO | 2007003961 A2 | 1/2007 |
| WO | 2007003962 A2 | 1/2007 |
| WO | 2007003964 a1 | 1/2007 |

(Continued)

OTHER PUBLICATIONS

Jones et al. Expert Opin. Ther. Patents (2009) 19(10):1339-1359.*
Freshney et al.,Culture of Animal Cells, A Manual of Basic Technique, Alan R. Liss, Inc., 1983, New York, p. 4.*
Dermer et al., Bio/Technology, 1994, 12:320.*
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.

(Continued)

*Primary Examiner* — Venkataraman Balasubramanian
(74) *Attorney, Agent, or Firm* — Michael P. Morris; David L. Kershner; Timothy X. Witkowski

(57) ABSTRACT

New compounds are disclosed which have utility in the treatment of a variety of metabolic related conditions in a patient. The compounds of this invention have the structure (I):

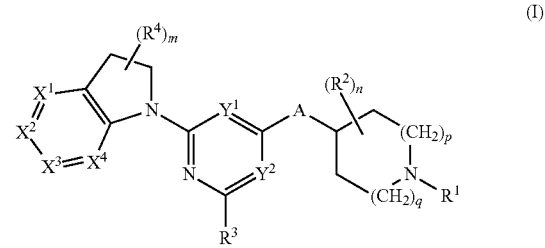

(I)

wherein $X^1, X^2, X^3, X^4, Y^1, Y^2, A, R^1, R^2, R^3, R^4$, m, n, p, and q are as defined herein, including stereoisomers, esters, and pharmaceutically acceptable salts thereof. Also disclosed are compositions containing a compound of this invention in combination with a pharmaceutically acceptable carrier, as well as methods relating to the use thereof in a patient in need thereof.

22 Claims, No Drawings

FOREIGN PATENT DOCUMENTS

| | | |
|---|---|---|
| WO | 2007035355 A2 | 3/2007 |
| WO | 2007109045 A1 | 9/2007 |
| WO | 2007116229 A1 | 10/2007 |
| WO | 2007116230 A1 | 10/2007 |
| WO | 2007120689 A2 | 10/2007 |
| WO | 2007120702 A2 | 10/2007 |
| WO | 2007138362 A1 | 12/2007 |
| WO | 2008005569 A2 | 1/2008 |
| WO | 2008005576 A1 | 1/2008 |
| WO | 2008008887 A2 | 1/2008 |
| WO | 2008008895 A1 | 1/2008 |
| WO | 2008009924 A2 | 1/2008 |
| WO | 2008025798 A1 | 3/2008 |
| WO | 2008025799 A1 | 3/2008 |
| WO | 2008025800 A1 | 3/2008 |
| WO | 2008070692 A2 | 6/2008 |
| WO | 2008081204 A1 | 7/2008 |
| WO | 2008081205 A1 | 7/2008 |
| WO | 2008081206 A1 | 7/2008 |
| WO | 2008081207 A1 | 7/2008 |
| WO | 2008081208 A1 | 7/2008 |
| WO | 2008083238 A2 | 7/2008 |
| WO | 2008097428 A2 | 8/2008 |
| WO | 2008109702 A1 | 9/2008 |
| WO | 2008120818 A1 | 10/2008 |
| WO | 2008137435 A1 | 11/2008 |
| WO | 2008137436 A1 | 11/2008 |
| WO | 2009012275 A1 | 1/2009 |
| WO | 2009012277 A1 | 1/2009 |
| WO | 2009014910 A2 | 1/2009 |
| WO | 2009034388 A1 | 3/2009 |
| WO | 2009038974 A1 | 3/2009 |
| WO | 2009050522 A1 | 4/2009 |
| WO | 2009050523 A1 | 4/2009 |
| WO | 2009051119 A1 | 4/2009 |
| WO | 2009055331 A2 | 4/2009 |
| WO | 2009073772 A1 | 6/2009 |
| WO | 2009105715 A1 | 8/2009 |
| WO | 2009105717 A1 | 8/2009 |
| WO | 2009106561 A1 | 9/2009 |
| WO | 2009106565 A1 | 9/2009 |
| WO | 2009123221 A1 | 10/2009 |
| WO | 2009123992 A1 | 10/2009 |
| WO | 2009125434 A2 | 10/2009 |
| WO | 2009126535 A1 | 10/2009 |
| WO | 2009129036 A1 | 10/2009 |
| WO | 2009141238 A1 | 11/2009 |
| WO | 2009150144 A1 | 12/2009 |
| WO | 2010004343 A1 | 1/2010 |
| WO | 2010004344 A1 | 1/2010 |
| WO | 2010004345 A1 | 1/2010 |
| WO | 2010004346 A1 | 1/2010 |
| WO | 2010004347 A1 | 1/2010 |
| WO | 2010004348 A1 | 1/2010 |
| WO | 2010006191 A1 | 1/2010 |
| WO | 2010008739 A2 | 1/2010 |
| WO | 2010009183 A1 | 1/2010 |
| WO | 2010009195 A1 | 1/2010 |
| WO | 2010013849 A1 | 2/2010 |
| WO | 2010014593 A1 | 2/2010 |
| WO | 2010048149 A2 | 4/2010 |
| WO | 2010074271 A1 | 7/2010 |
| WO | 2010075269 A1 | 7/2010 |
| WO | 2010075271 A1 | 7/2010 |
| WO | 2010075273 A1 | 7/2010 |
| WO | 2010084512 A1 | 7/2010 |
| WO | 2010084944 A1 | 7/2010 |
| WO | 2010088518 A2 | 8/2010 |
| WO | 2010095663 A1 | 8/2010 |
| WO | 2010103333 A1 | 9/2010 |
| WO | 2010103334 A1 | 9/2010 |
| WO | 2010103335 A1 | 9/2010 |
| WO | 2010106457 A2 | 9/2010 |
| WO | 2010114957 A1 | 10/2010 |
| WO | 2010114958 A1 | 10/2010 |
| WO | 2010123018 A1 | 10/2010 |
| WO | 2010128414 A1 | 11/2010 |
| WO | 2010128425 A1 | 11/2010 |
| WO | 2010135505 A2 | 11/2010 |
| WO | 2010135506 A1 | 11/2010 |
| WO | 2010140092 A1 | 12/2010 |
| WO | 2010149684 A1 | 12/2010 |
| WO | 2010149685 A1 | 12/2010 |
| WO | 2011138427 A2 | 11/2011 |
| WO | 2012072505 A1 | 6/2012 |
| WO | 2012080476 A1 | 6/2012 |
| WO | 2012098217 A1 | 7/2012 |
| WO | 2012123449 A1 | 9/2012 |

OTHER PUBLICATIONS

Abstract in English for WO2010013849 publication date Feb. 4, 2010.
Abstract in English for WO2010074271 publication date Jul. 1, 2010.
Abstract in English for WO2010084944 publication date Jul. 29, 2010.
Abstract in English for WO2010095663 publication date Aug. 26, 2010.
Abstract in English for WO2010123018 publication date Oct. 28, 2010.
Abstract in English for WO09123221 (2009) is AU2009232721 (2009) NPL.
Chu, Z-L, et al., "A Role for Intestinal Endocrine Cell-Expressed GPR119 in Glycemic Control by Enhancing GLP-1 and GIP Release". The Endocrine Socieity, Endocrinology, first published ahead of print Jan. 17, 2008.
Endocrinology. "G Protein-Coupled Receptors and Isuli Secretion: 119 and Counting". Endocrinology, 2007, 148, 6, p. 2598-2600.
International Search Report for PCT/EP2010/058874 mailed Sep. 23, 2010.
Overton, H.A. et al., "GPR119, a novel G protein-coupled receptor target for the treatment of type 2 diabetes and obesity". Life Sciences 2007, British Journal of Pharmacology, 2007, p. 1-6.
Sakamoto, Y. et al., Expression and distribution of Gpr119 in the pancreatic islets of mice and rats; predominant localization in pancreatic polypeptide-secreting PP-cells. Science Direct, Biochemical and Biophysical Research Communications, 351, 2006, p. 474-480.
Soga, T. et al., "Lysophosphatidylcholine enhances glucose-dependent insulin secretion via an orphan G-protein-coupled receptor". Science Direct, Biochemical and Biophysical Research Communications, 326, 2005, p. 744-751.
Winzell, M.S., et al. "G-protein-coupled receptors and islet function—Implications for treatment of type 2 diabetes". Science Direct, Pharmacology and Therapeutics, 116, 2007, p. 437-448.
WO200800839 (Part 1of2), International Publication Date: Jan. 17, 2008. Patentee: Shionogi & Co. Ltd. Inventor: A, Matsumura, Title: Oxime Compounds and their use thereof. Total pp. 599. Part 1 of 2. This foreign patent is too large for EFS submission via the Foreign patent section. Therefore filing in two parts in the NPL section. pp. 1-319.
WO200800839 (Part 2of2), International Publication Date: Jan. 17, 2008. Patentee: Shionogi & Co. Ltd. Inventor: A, Matsumura, Title: Oxime Compounds and their use thereof. Total pp. 599. Part 2 of 2. This foreign patent is too large for EFS submission via the Foreign patent section. Therefore filing in two parts in the NPL section. pp. 319-599.

* cited by examiner

COMPOUNDS, PHARMACEUTICAL COMPOSITION AND METHODS RELATING THERETO

FIELD OF THE INVENTION

This invention relates generally to new compounds of the formula (I), to pharmaceutical compositions and to methods of treating diseases and conditions by administration of such compounds to a patient in need thereof.

BACKGROUND OF THE INVENTION

Diabetes is an increasingly prevalent chronic disease whose impact as a public health concern is felt throughout the world. The American Diabetes Association estimates approximately 7% of the United States population suffers from this disease and that 1 out of every 10 dollars spent on healthcare in the U.S. is spent on diabetes and its complications. Type 1 diabetes generally results from the body's failure to produce insulin. Type 2 diabetes is the more prevalent type of diabetes and generally results from insulin resistance combined with a relative insulin deficiency. Additionally, there are millions of Americans who can be said to have prediabetes, that is, higher than normal blood glucose levels but not yet high enough to be diagnosed with Type 2 diabetes.

Type 2 diabetes is characterized by fasting and postprandial hyperglycemia and by relative insulin insufficiency. Hyperglycemia may cause long-term microvascular and macrovascular complications, such as nephropathy, neuropathy, retinopathy, and peripheral vascular disease. In addition, Type 2 diabetes is a comorbid disease that frequently compounds hyperlipidemia, atherosclerosis and hypertension. Hyperlipidemia is a primary risk factor for cardiovascular disease due to atherosclerosis. Obesity is a well known common risk factor for the development of atherosclerosis, stroke, hypertension and Type 2 diabetes. Type 2 diabetes causes significant morbidity and mortality at considerable expense to patients, their families and society. Furthermore, the incidence of Type 2 diabetes worldwide is increasing such that Type 2 diabetes is now considered to be a worldwide epidemic.

A number of therapies for the treatment of Type II diabetes are in use. A change in diet along with an increase in exercise and weight loss is considered a first line of treatment. However, this may not result in sufficient control of blood glucose levels resulting in the use of medications to help control glucose levels. These medications include insulin, sulfonylureas, meglitinides, biguanides, thiazolidinediones, DPP-4 inhibitors, alpha-glucosidase inhibitors, amylin analogs and incretin mimetics. These medications may be used singly or in combination and may result in reduced glucose levels. However, these medications still may not cause a drop in glucose levels to what would be considered normal or the effect may wear off over time. Some medications may lower glucose levels too much, resulting in a dangerous hypoglycemic episode. Insulin, amylin and incretin mimetics need to be injected, often numerous times a day. Other side effects include weight gain, nausea, and diarrhea.

GPR119 is a class 1 G-protein-coupled receptor which has received attention due to evidence that modulation of the GRP119 receptor may produce favorable effects on glucose homeostasis, food intake, body weight gain and β-cell preservation, any or all of which effects may be useful in the treatment of both diabetes and obesity (Br. J. Pharm. 2007 1-6).

The GPR119 receptor and isoforms have been identified in mammalian species including human, rat, mouse, hamster, chimpanzee, rhesus monkey, cattle and dog. The pancreas has been identified as the major site of mRNA expression in the human, with some expression also seen in the gastrointestinal tract. The expression of GPR119 in the pancreas and particularly in the pancreatic β-cells led to the hypothesis that the GPR119 receptor could have effects upon insulin secretion.

The discovery of two endogenous ligands, lysophosphatidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm 2005 744-751, Cell Metabolism 2006 167-175, Endocrinology 2007, 2601-9, Endocrinology, 2008, Epub ahead of print). GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Taken together, GPR119 is a novel mechanism by which glycemic control may be facilitated with the added benefit of weight loss.

BRIEF SUMMARY OF THE INVENTION

In brief, this invention is generally directed to new compounds, as well as to methods for their preparation and use, and to pharmaceutical compositions containing the same. More specifically, the new compounds are useful as GPR119 receptor agonists. In a first aspect the present invention relates to a compound of the following general formula (I):

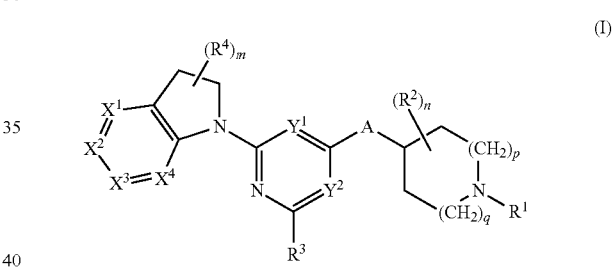

(I)

including tautomers and stereoisomers thereof, or a salt thereof, wherein $X^1$, $X^2$, $X^3$, $X^4$, $Y^1$, $Y^2$, A, $R^1$, $R^2$, $R^3$, $R^4$, m, n, p, and q are as defined below.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

The compounds of this invention may have utility over a wide range of therapeutic applications, and may be used to treat a variety of diseases and conditions in both men and women, as well as a mammal in general (also referred to herein as a "patient"). For example, such conditions include diabetes and obesity. The compounds of the present invention may treat these conditions through effects on glucose homeostasis, food intake, body weight gain and beta-cell preservation.

Therefore in a further aspect this invention relates to a method for treating diseases or conditions which are mediated by modulating the activity of GPR119 enzyme(s) in a patient in need thereof characterized in that a compound of general formula (I) or a pharmaceutically acceptable salt thereof is administered to a patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided the use of a compound of the general formula (I) or a physiologically acceptable salt thereof for the manufacture of a medicament for a therapeutic method as described hereinbefore and hereinafter.

The methods of this invention include administering an effective amount of a compound of this invention, preferably in the form of a pharmaceutical composition, to a patient in need thereof.

In a further aspect this invention relates to a pharmaceutical composition, comprising one or more compounds of general formula (I) or one or more pharmaceutically acceptable salts thereof according to the invention, optionally together with one or more pharmaceutically acceptable carriers and/or diluents.

Compounds of the present invention may be administered along with additional agents, for example to help lower glucose levels. Additional therapeutic agents which may be used in conjunction with a compound of the current invention include insulin, sulfonylureas, meglitinides, biguanides, thiazolidinediones, DPP-4 inhibitors, alpha-glucosidase inhibitors, amylin analogs and incretin mimetics.

Therefore in a further aspect this invention relates to a method for treating a disease or condition mediated by modulating the activity of GPR119 in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) in combination with one or more additional therapeutic agents for the treatment or prevention of diseases or conditions which are mediated by modulating the activity of GPR119.

In a further aspect this invention relates to a pharmaceutical composition which comprises a compound according to general formula (I) and one or more additional therapeutic agents, optionally together with one or more pharmaceutically acceptable carriers and/or diluents.

These and other aspects of the invention will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE INVENTION

As mentioned above, the present invention is directed generally to compounds useful as GPR119 receptor agonists. The compounds of this invention have the following structure (I):

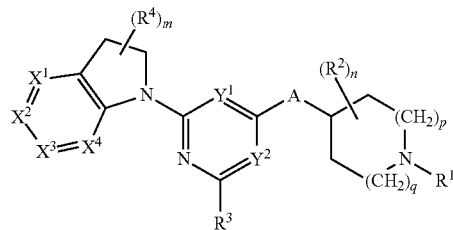

(I)

wherein:
$X^1$, $X^2$, $X^3$, and $X^4$ are independently —N— or —C($R^5$)—;

$Y^1$ and $Y^2$ are independently —N— or —C($R^3$)—;
A is —O— or —N($R^7$)—;
$R^1$ is $R^{Alk}$, aryl-$C_{1-4}$alkyl, heterocycle-$C_{1-4}$alkyl, —C(=O)$R^7$, —CO$_2R^6$, —SO$_2R^6$, —C(=O)N($R^7$)$_2$, —C(=S)N($R^7$)$_2$, aryl, or heterocycle, wherein each $R^{Alk}$, alkyl, aryl and heterocycle is optionally substituted with 1-4 substituents independently of each other selected from $R^9$;
$R^2$ at each occurrence is independently $C_{1-4}$alkyl, F, hydroxy, or $C_{1-4}$alkyl-O—;
$R^3$ at each occurrence is independently H, halogen, CN, $C_{1-4}$alkyl, $C_{1-4}$alkyl-O— or $C_{1-4}$alkyl-S—;
$R^4$ at each occurrence is independently H, halogen, or $C_{1-4}$alkyl;
$R^5$ at each occurrence is independently H, halogen, cyano, hydroxy, $R^{Alk}$, halo$C_{1-4}$alkyl, —NO$_2$, —C(=O)$R^6$, —CO$_2R^6$, —C(=O)N($R^7$)$_2$, —SO$_2$N($R^7$)$_2$, —S(=O)$R^6$, —S(=O)$_2R^6$, $C_{1-6}$alkyl-O—, halo$C_{1-4}$alkyl-O—, —N($R^7$)$_2$, $C_{1-6}$alkyl-S—, aryl, aryl-$C_{1-6}$alkyl, heterocycle, heterocycle-$C_{1-6}$alkyl, —N$R^7$C(=O)$R^6$, —N$R^7$C(=O)N($R^7$)$_2$, —N$R^7$C(=O)O$R^7$, —N$R^7$C(=N$R^7$)N($R^7$)$_2$, or —N$R^7$S(=O)$_2$N($R^7$)$_2$ wherein each $R^{Alk}$, alkyl, aryl, and heterocycle is optionally substituted with 1-5 substituents independently of each other selected from $R^9$;
$R^6$ is $R^{Alk}$, heterocycle, heterocycle-$C_{1-3}$-alkyl or aryl, wherein each $R^{Alk}$, alkyl, heterocycle and aryl is optionally substituted with 1-4 substituents independently of each other selected from $R^9$;
$R^7$ at each occurrence is independently H or $R^{Alk}$ wherein each $R^{Alk}$ is optionally substituted with 1-4 substituents independently of each other selected from halogen, hydroxy, —N($R^8$)$_2$, $C_{1-4}$alkyl-O—, and —CO$_2R^8$;
$R^8$ at each occurrence is independently H or $C_{1-4}$alkyl;
$R^9$ is at each occurrence is independently cyano, hydroxy, $R^{Alk}$, aryl, aryl-$C_{1-3}$-alkyl, heterocycle, halogen, oxo, $C_{1-4}$haloalkyl, —NO$_2$, —C(=O)H, —CO$_2R^8$, —OC(=O)$R^{Alk}$, —C(=O)N($R^7$)$_2$, —SO$_2$N($R^7$)$_2$, —S(=O)$R^{Alk}$, —S(=O)$_2R^{Alk}$, $C_{1-6}$alkyl-O—, halo$C_{1-4}$alkyl-O—, —N($R^7$)$_2$, —S$R^7$, —N$R^7$C(=O)$R^{Alk}$, —N$R^7$C(=O)O$R^{Alk}$ or —N$R^7$C(=O)N($R^7$)$_2$, wherein each $R^{Alk}$, alkyl, aryl and heterocycle is optionally substituted with 1-4 substituent independently of each other selected from halogen, hydroxy, —N($R^8$)$_2$, $C_{1-4}$alkyl-O—, —N$R^7$CO$_2R^7$, —N$R^7$SO$_2R^7$, and —CO$_2R^8$;
$R^{Alk}$ at each occurrence is independently $C_{1-6}$-alkyl, $C_{2-6}$-alkenyl, $C_{2-6}$-alkynyl, $C_{3-8}$-cycloalkyl, $C_{3-8}$-cycloalkyl-$C_{1-3}$-alkyl, $C_{4-8}$-cycloalkenyl or $C_{4-8}$-cycloalkenyl-$C_{1-3}$-alkyl;
m is 0, 1, or 2;
n is 0, 1, or 2;
p is 0 or 1; and
q is 0, 1, or 2,
including any tautomers and stereoisomers thereof,
or a salt thereof.

Unless otherwise stated, the groups, residues, and substituents, particularly $X^1$, $X^2$, $X^3$, $X^4$, $Y^1$, $Y^2$, A, $R^1$, $R^2$, $R^3$, $R^4$, $R^5$, $R^6$, $R^7$, $R^8$, $R^9$, and the indexes, particularly m, n, p, q, are defined as above and hereinafter. If residues, substituents, or groups occur several times in a compound, as for example $R^{Alk}$, $R^6$, $R^7$, $R^8$, $R^9$, they may have the same or different meanings. Some preferred meanings of individual groups and substituents of the compounds according to the invention will be given hereinafter. Any and each of these definitions may be combined with each other.

$X^1$, $X^2$, $X^3$, $X^4$:

According to an embodiment X-E1 the groups $X^1$, $X^2$, $X^3$, and $X^4$ are independently —N—, —CH— or —C($R^5$)—.

According to an embodiment X-E1a the groups $X^1$, $X^2$, $X^3$, and $X^4$ are independently —N—, —CH— or —C($R^5$)—, wherein at least one of $X^1$, $X^2$, $X^3$, and $X^4$ is —$C(R^5)$—, wherein $R^5$ is defined as hereinbefore and hereinbefore, but does not denote hydrogen.

According to an embodiment X-E2 the groups $X^1$, $X^2$, $X^3$, and $X^4$ are independently —CH— or —$C(R^5)$—, wherein $R^5$ is defined as hereinbefore and hereinbefore, but does not denote hydrogen.

According to an embodiment X-E2a the groups $X^1$, $X^2$, $X^3$, and $X^4$ are independently —CH— or —$C(R^5)$—, wherein at least one of $X^1$, $X^2$, $X^3$, and $X^4$ is —$C(R^5)$—, wherein $R^5$ is defined as hereinbefore and hereinbefore, but does not denote hydrogen.

According to an embodiment X-E3 the groups $X^1$, $X^3$, and $X^4$ are —CH— and $X^2$ is —$C(R^5)$— wherein $R^5$ is defined as hereinbefore and hereinbefore, but does not denote hydrogen.

$Y^1, Y^2$:

According to an embodiment Y-E1 the groups $Y^1$ and $Y^2$ are independently —N— or —$C(R^3)$—.

According to an embodiment Y-E2 the group $Y^1$ is —$C(R^{31})$— and $Y^2$ is N or —$C(R^{32})$—, wherein $R^{31}$ and $R^{32}$ are defined as $R^3$. According to one aspect of this embodiment $R^{31}$ and $R^{32}$ independently of each other denote H, F, CN, $C_{1-3}$-alkyl or $C_{1-3}$-alkyl-O—.

According to an embodiment Y-E3 the group $Y^1$ is —$C(R^{31})$— and $Y^2$ is N, wherein $R^{31}$ is defined as $R^3$. According to one aspect of this embodiment $R^{31}$ denotes H, F, CN, $C_{1-3}$-alkyl or $C_{1-3}$-alkyl-O—, in particular H, F, $CH_3$, —O—$CH_3$. According to another aspect of this embodiment $R^{31}$ denotes H.

A:

According to an embodiment A-E1 the group A denotes —O— or —$N(R^7)$—.

According to an embodiment A-E2 the group A denotes —O—.

According to an embodiment A-E3 the group A denotes —$NR^7$—, wherein $R^7$ denotes H, $C_{1-4}$-alkyl, $C_{3-4}$-alkenyl, $C_{1-3}$-alkyl-O—$C_{1-3}$-alkyl.

According to an embodiment A-E3a the group A denotes —NR—, wherein $R^7$ denotes H, methyl, ethyl, sec-butyl, allyl, $CH_3$—O—$CH_2$—.

p, q:

According to an embodiment pq-E1 the index p is 0 or 1 and the index q is 0, 1 or 2.

According to an embodiment pq-E2 the index p is 1 and the index q is 1.

According to an embodiment pq-E3 the index p is 0 and the index q is 0.

m, n:

According to an embodiment mn-E1 the index m is 0, 1 or 2 and the index n is 0, 1 or 2.

According to an embodiment mn-E2 the index m is 1 and the index n is 0.

$R^1$:

According to an embodiment $R^1$-E1 the group $R^1$ denotes $C_{1-6}$alkyl, aryl-$C_{1-4}$alkyl, heterocycle-$C_{1-4}$alkyl, —C(=O)$R^7$, —$CO_2R^6$, —$SO_2R^6$, —C(=O)$N(R^7)_2$, —C(=S)$N(R^7)_2$, aryl, or heterocycle, wherein each $C_{1-6}$alkyl, aryl and heterocycle are optionally substituted with 1-4 substituents independently of each other selected from $R^9$.

According to an embodiment $R^1$-E2 the group $R^1$ denotes —$CO_2R^6$,

According to an embodiment $R^1$-E3 the group $R^1$ denotes $C_{1-6}$-alkyl-O—C(=O)—, $C_{3-6}$-cycloalkyl-O—C(=O)—, $C_{3-6}$-cycloalkyl-$C_{1-3}$-alky-O—C(=O)—, heterocycle-O—C(=O)—, wherein each alkyl, cycloalkyl and heterocycle group is optionally substituted with 1 to 4 substituents independently of each other selected from F and $C_{1-3}$-alkyl-O—, and wherein heterocycle is selected from azetidinyl, pyrrolidinyl, piperidinyl and azepanyl, wherein the heterocycle group is optionally substituted with $C_{1-4}$-alkyl or phenyl-$CH_2$—, wherein the phenyl ring is optionally substituted with 1 to 5 substituents independently of each other selected from halogen, in particular F.

According to an embodiment $R^1$-E3a the group $R^1$ denotes $C_{1-6}$-alkyl-O—C(=O)—, $C_{3-6}$-cycloalkyl-O—C(=O)—, $C_{3-6}$-cycloalkyl-$C_{1-3}$-alky-O—C(=O)—, wherein each alkyl and cycloalkyl group is optionally substituted with 1 to 4 substituents independently of each other selected from F and $C_{1-3}$-alkyl-O.

According to an embodiment $R^1$-E4a the group $R^1$ is selected from

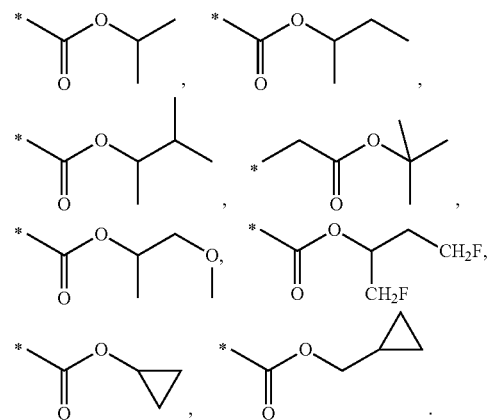

According to an embodiment $R^1$-E4b the group $R^1$ is selected from

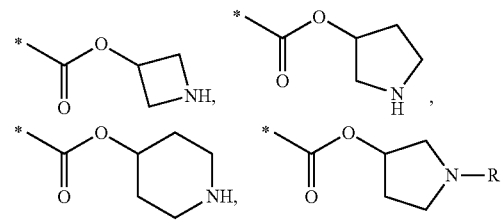

wherein R is benzyl, which is optionally substituted by 1 to 5 F-atoms.

$R^2$:

According to an embodiment $R^2$-E1 the group $R^2$ denotes at each occurrence independently $C_{1-4}$alkyl, F, hydroxy or $C_{1-4}$alkyl-O—.

$R^3$:

According to an embodiment $R^3$-E1 the group $R^3$ denotes H, halogen, CN, $C_{1-4}$alkyl, $C_{1-4}$alkyl-O—, or $C_{1-4}$alkyl-S—.

According to an embodiment $R^3$-E2 the group $R^3$ denotes H, Cl, methyl, methylthio.

According to an embodiment $R^3$-E3 the group $R^3$ denotes H.

$R^4$:

According to an embodiment $R^4$-E1 the group $R^4$ denotes at each occurrence independently H, halogen, or $C_{1-4}$alkyl.

$R^5$:

According to an embodiment $R^5$-E1 the group $R^5$ denotes at each occurrence independently H, halogen, cyano, hydroxy, $C_{1-6}$alkyl, halo$C_{1-4}$alkyl, —$NO_2$, —C(=O)$R^6$, —CO$_2$R$^6$, —C(=O)N(R$^7$)$_2$, —SO$_2$N(R$^7$)$_2$, —S(=O)R$^6$, —S(=O)$_2$R$^6$, C$_{1-6}$alkyl-O—, haloC$_{1-4}$alkyl-O—, —N(R$^7$)$_2$, C$_{1-6}$alkyl-S—, aryl, aryl-C$_{1-6}$alkyl, heterocycle, heterocycle-C$_{1-6}$alkyl, —NR$^7$C(=O)R$^6$, —NR$^7$C(=O)N(R$^7$)$_2$, —NR$^7$C(=O)OR$^7$, —NR$^7$C(=NR$^7$)N(R$^7$)$_2$, or —NR$^7$S(=O)$_2$N(R$^7$)$_2$ wherein each C$_{1-6}$alkyl, aryl and heterocycle are optionally substituted with 1-5 R$^9$.

According to an embodiment R$^5$-E2 the group R$^5$ denotes at each occurrence independently halogen, —NO$_2$, —S(=O)$_2$R$^6$, —CO$_2$R$^6$.

According to an embodiment R$^5$-E3 the group R$^5$ denotes at each occurrence independently halogen, —NO$_2$, —S(=O)$_2$—C$_{1-4}$-alkyl.

According to an embodiment R$^5$-E3 the group R$^5$ denotes at each occurrence independently F, Cl, —NO$_2$, —S(=O)$_2$—CH$_3$.

R$^6$:

According to an embodiment R$^6$-E1 the group R$^6$ denotes C$_{1-6}$-alkyl, C$_{3-7}$-cycloalkyl, C$_{3-7}$-cycloalkyl-C$_{1-3}$-alkyl, heterocycle, heterocycle-C$_{1-3}$-alkyl, wherein each of the beforementioned group is optionally substituted with 1 to 4 substituents independently of each other selected from R$^9$.

According to an embodiment R$^6$-E2 the group R$^6$ denotes C$_{1-4}$-alkyl, C$_{3-6}$-cycloalkyl, C$_{3-6}$-cycloalkyl-C$_{1-3}$-alkyl, wherein each of the beforementioned group is optionally substituted with 1 to 4 substituents independently of each other selected from R$^9$, in particular selected from F and C$_{1-3}$-alkyl-O—.

According to an embodiment R$^6$-E3 the group R$^6$ denotes i-propyl, sec-butyl, tert-butyl, cyclopropyl, cycloproyl-methyl-, all of which optionally substituted with one or more F, C$_{1-3}$-alkyl-O—, According to an embodiment R$^6$-E4 the group R$^6$ denotes heterocycle which is selected from azetidinyl, pyrrolidinyl, piperidinyl and azepanyl, wherein the heterocycle group is optionally substituted with 1 to 4 substituents independently of each other selected from R$^9$, in particular selected from C$_{1-3}$-alkyl and phenyl-C$_{1-3}$-alkyl, wherein the phenyl ring is optionally substituted with 1-4 substituents independently of each other selected from F, C$_{1-3}$-alkyl-, C$_{1-3}$-alkyl-O—.

R$^7$:

According to an embodiment R$^7$-E1 the group R$^7$ denotes H or R$^{Alk}$ wherein said R$^{Alk}$ is optionally substituted with 1-4 substituents independently of each other selected from halogen, hydroxy, —N(R$^8$)$_2$, C$_{1-4}$alkoxy, and —CO$_2$R$^8$;

According to an embodiment R$^7$-E2 the group R$^7$ denotes H, C$_{1-4}$-alkyl, C$_{3-4}$-alkenyl, C$_{1-3}$-alkyl-O—C$_{1-3}$-alkyl.

According to an embodiment R$^7$-E2a the group R$^7$ denotes H, C$_{1-4}$-alkyl, C$_{3-4}$-alkenyl.

R$^8$:

According to an embodiment R$^8$-E1 the group R$^8$ denotes H or C$_{1-4}$alkyl.

R$^9$:

According to an embodiment R$^9$-E1 the group R$^9$ denotes cyano, hydroxy, C$_{1-6}$alkyl, aryl, aryl-C$_{1-3}$-alkyl, heterocycle, halogen, oxo, C$_{1-4}$haloalkyl, —NO$_2$, —C(=O)H, —CO$_2$R$^8$, —OC(=O)R$^{Alk}$, —C(=O)N(R$^7$)$_2$, —SO$_2$N(R$^7$)$_2$, —S(=O)R$^{Alk}$, —S(=O)$_2$R$^{Alk}$, C$_{1-6}$alkyl-O—, haloC$_{1-4}$alkyl-O—, —N(R$^7$)$_2$, —SR$^7$, —NR$^7$C(=O)R$^{Alk}$, —NR$^7$C(=O)OR$^{Alk}$ or —NR$^7$C(=O)N(R$^7$)$_2$, wherein each alkyl, aryl and heterocycle is optionally substituted with 1-4 substituent independently of each other selected from halogen, hydroxy, —N(R$^8$)$_2$, C$_{1-4}$alkoxy, —NR$^7$CO$_2$R$^7$, —NR$^7$SO$_2$R$^7$, and —CO$_2$R$^8$.

R$^{Alk}$:

According to an embodiment R$^{Alk}$-E1 the group R$^{Alk}$ is selected from the group consisting of C$_{1-6}$-alkyl, C$_{2-6}$-alkenyl, C$_{2-6}$-alkynyl, C$_{3-8}$-cycloalkyl, C$_{3-8}$-cycloalkyl-C$_{1-3}$-alkyl, C$_{4-8}$-cycloalkenyl or C$_{4-8}$-cycloalkenyl-C$_{1-3}$-alkyl.

According to an embodiment R$^{Alk}$-E2 the group R$^{Alk}$ is selected from the group consisting of C$_{1-6}$-alkyl, C$_{3-7}$-cycloalkyl or C$_{3-7}$-cycloalkyl-C$_{1-3}$-alkyl.

According to an embodiment R$^{Alk}$-E3 the group R$^{Alk}$ is selected from the group consisting of C$_{1-4}$-alkyl, C$_{3-6}$-cycloalkyl or C$_{3-6}$-cycloalkyl-CH$_2$—.

The following embodiments of compounds of the formula (I) are described using generic formulas (I), (I.1) to (I.6), (II), (III), (IV), (V), (VI) and (VII), wherein any tautomers and stereoisomers, esters, and salts thereof, in particular the pharmaceutically acceptable salts, are encompassed.

In an embodiment of the present invention, $X^1$, $X^3$, and $X^4$ of structure (I) are —C(R$^5$)— where R$^5$ is H, X$^2$ is —C(R$^5$)— and A is O as shown in structure (II). Structure (III) shows an embodiment of structure (II) where Y$^1$ is —C(R$^3$)— and R$^3$ is H, and Y$^2$ is N.

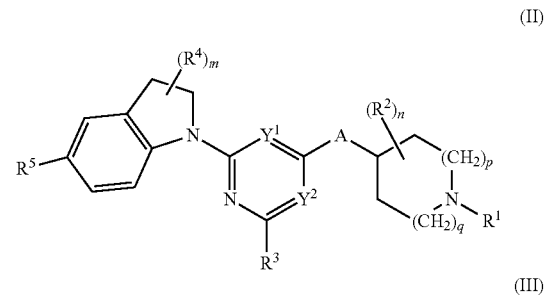

(II)

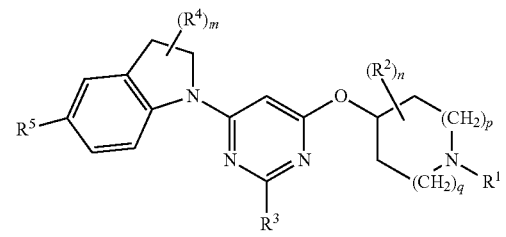

(III)

In an further embodiment of structure (III), m and n are 0, p and q are 1, and R$^1$ is —CO$_2$R$^6$ as shown in structure (IV). In an embodiment of structure (I), A is —N(R$^7$)— and Y$^1$ and Y$^2$ are —C(R$^3$)— where R$^3$ is H as shown in structure (V).

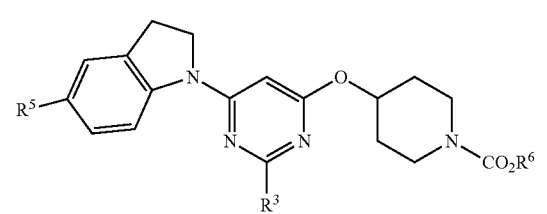

(IV)

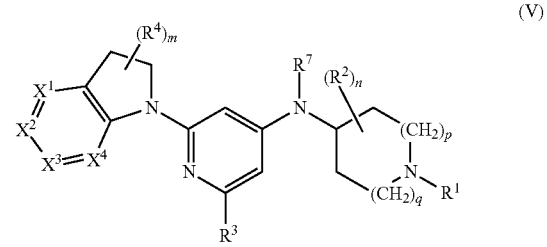

(V)

In an embodiment of structure (I), m and n are 0, p and q are 1, and A is NR$^7$ as shown in structure (VI). In an embodiment of structure (VI), $Y^1$ is —C($R^3$)— where $R^3$ is H, and $R^1$ is —$CO_2R^6$ as shown in structure (VII).

(VI)
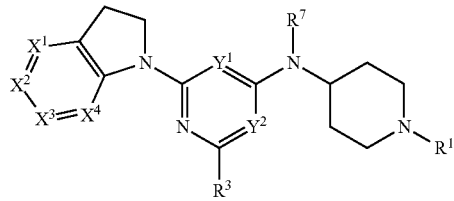

(VII)
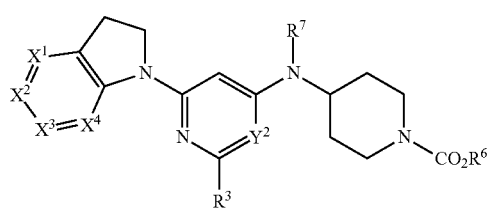

Further embodiments of compounds of the present invention are depicted by the following structural formulas (I.1)
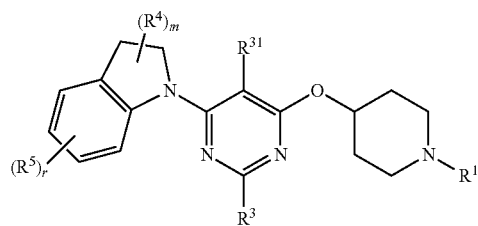

(I.2)
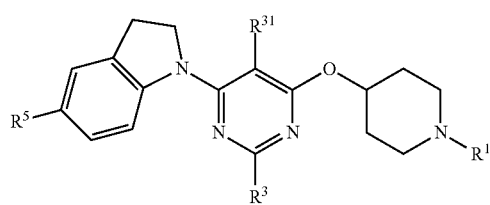

(I.3)
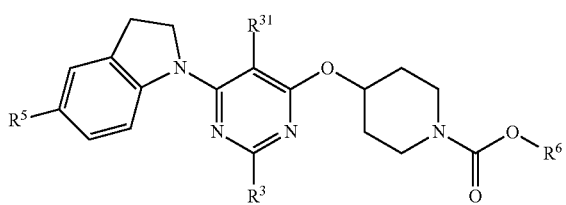

(I.4)
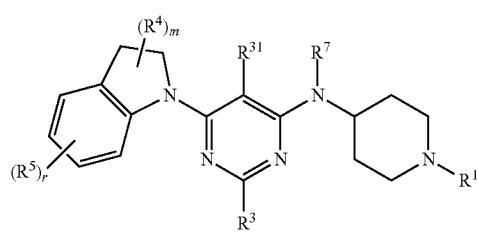

(I.5)
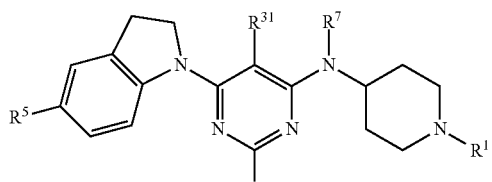

(I.6)
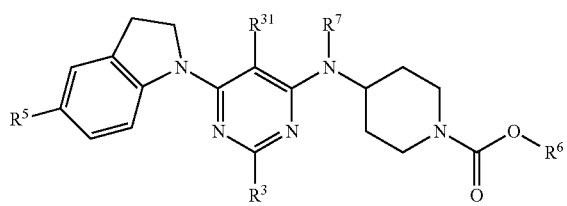

including tautomers, stereoisomers and esters thereof, and salts, particularly pharmaceutically acceptable salts, thereof, wherein in each of the formulas (I), (I.1) to (I.6), (II), (III), (IV), (V), (VI) and (VII) the groups $X^1$, $X^2$, $X^3$, $X^4$, $Y^1$, $Y^2$, $R^1$, $R^2$, $R^3$, $R^{31}$, $R^4$, $R^5$, $R^6$, $R^7$, and the indexes m, n, p, q are defined as hereinbefore and hereinafter; and wherein r is 0 to 4, in particular r is 1;

$X^1$, $X^2$, $X^3$, and $X^4$ are selected from an embodiment X-E1, X-E1a, X-E2, X-E2a or X-E3;

$R^1$ is selected from an embodiment $R^1$-E1, $R^1$-E2, $R^1$-E3, $R^1$-E3a, $R^1$-E4a or $R^1$-E4b; and $R^2$ is selected from an embodiment $R^1$-E1; and $R^3$ is selected from an embodiment $R^3$-E1, $R^3$-E2 or $R^3$-E3; and $R^{31}$ is selected from the definitions of the group $R^3$ as described in $R^3$-E1, $R^3$-E2 or $R^3$-E3 or $R^{31}$ denotes H, F, CN, $C_{1-3}$-alkyl or $C_{1-3}$-alkyl-O—.

$R^4$ is selected from an embodiment $R^4$-E1; and $R^5$ is selected from an embodiment $R^5$-E1, $R^5$-E2 or $R^5$-E3; and $R^6$ is selected from an embodiment $R^6$-E1, $R^6$-E2, $R^6$-E3 or $R^6$-E4; and $R^7$ is selected from an embodiment $R^7$-E1 or $R^7$-E2; and m, n are selected from an embodiment mn-E1 or mn-E2; and p, q are selected from an embodiment pq-E1, pq-E2 or pq-E3.

Examples of particular subgeneric embodiments according to the present invention are set forth in the following table, wherein each substituent group of each embodiment is defined according to the definitions set forth hereinbefore and wherein all other substituents of the given formula are defined according to the definitions set forth hereinbefore:

| Embodiment | Formula | $R^5$ | $R^3$ | $R^7$ | $R^1$ | $R^6$ |
|---|---|---|---|---|---|---|
| E-1 | I.1 | $R^5$-E1 | $R^3$-E1 | — | $R^1$-E1 | — |
| E-2 | I.1 | $R^5$-E3 | $R^3$-E3 | — | $R^1$-E3a | — |
| E-3 | I.2 | $R^5$-E1 | $R^3$-E1 | — | $R^1$-E1 | — |
| E-4 | I.2 | $R^5$-E3 | $R^3$-E3 | — | $R^1$-E3a | — |
| E-5 | I.3 | $R^5$-E3 | $R^3$-E3 | — | — | $R^6$-E1 |
| E-6 | I.3 | $R^5$-E3 | $R^3$-E3 | — | — | $R^6$-E2 |
| E-7 | I.4 | $R^5$-E1 | $R^3$-E1 | $R^7$-E1 | $R^1$-E1 | — |
| E-8 | I.4 | $R^5$-E3 | $R^3$-E3 | $R^7$-E2 | $R^1$-E3a | — |
| E-9 | I.5 | $R^5$-E1 | $R^3$-E1 | $R^7$-E1 | $R^1$-E1 | — |
| E-10 | I.5 | $R^5$-E3 | $R^3$-E3 | $R^7$-E2 | $R^1$-E3a | — |
| E-11 | I.6 | $R^5$-E3 | $R^3$-E3 | $R^7$-E1 | — | $R^6$-E1 |
| E-12 | I.6 | $R^5$-E3 | $R^3$-E3 | $R^7$-E2 | — | $R^6$-E2 | in the above embodiments m is 0, 1 or 2, preferably m is 0, and r is 0, 1 or 2, preferably r is 1, and $R^{31}$ is selected from the definitions of the $R^3$-E1 or $R^{31}$ denotes H, F, CN, $C_{1-3}$-alkyl or $C_{1-3}$-alkyl-O—, or $R^{31}$ denotes H;

including their tautomers and stereoisomers, and the salts thereof.

Particularly preferred compounds, including their tautomers and stereoisomers, and the salts thereof are described in the experimental section hereinafter.

The compounds of the present invention may be prepared by known organic synthesis techniques, including the methods described in more detail in the Examples. In general, the compounds of structure (I) above may be made by the following reaction schemes, wherein all substituents are as defined above unless indicated otherwise.

SCHEME 1

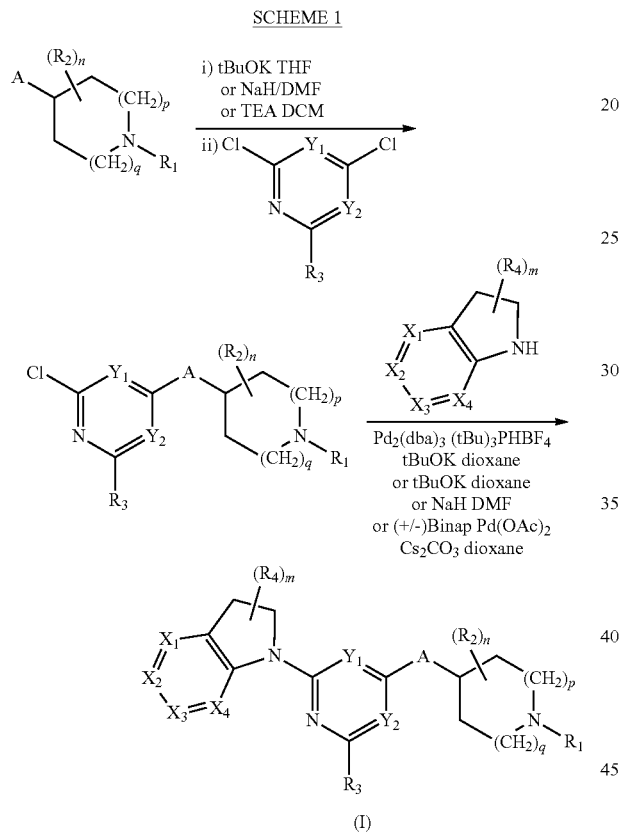

The compounds are prepared by O or N-arylation of a cyclic amino alcohol or amine with a dichloroheteroaryl (typically by nucleophilic aromatic displacement of a chloride in presence of a base), followed by reaction of the mono heteroaryl chloride obtained with indoline (either by palladium catalyzed coupling or nucleophilic displacement in presence of a base).

SCHEME 2

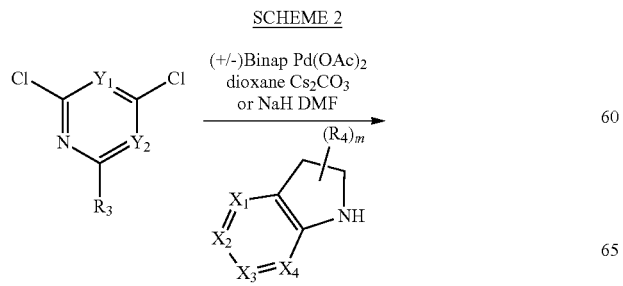

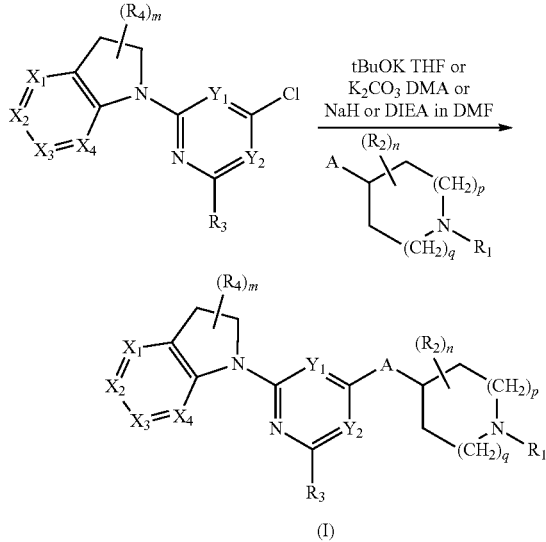

The compounds can also be prepared by reaction of the indoline with the dichloroheteroaryl first (by palladium catalyzed coupling or nucleophilic displacement in presence of a base), followed by O or N-arylation of a cyclic amino alcohol or amine with the monochloroheteroaryl obtained (typically by nucleophilic aromatic displacement in presence of a base).

SCHEME 3

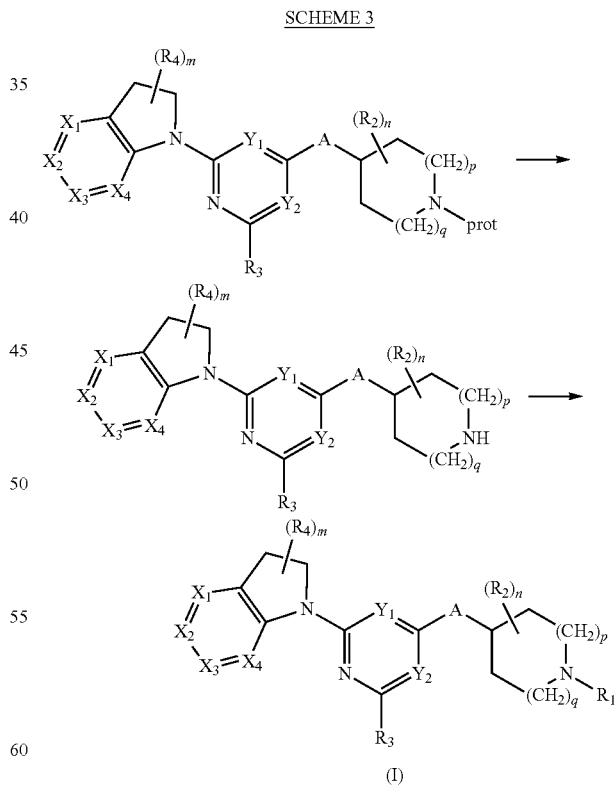

In the case where $R^1$ is a protecting group such as Boc or benzyl, the amine can be deprotected (typically with TFA for Boc and AceCl or hydrogenation for benzyl) and the amine further derivatized (for example by alkylation).

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention", "GPR119 receptor agonist(s) according to the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the modulation of the activity of the GPR119 enzyme(s) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk or the sign 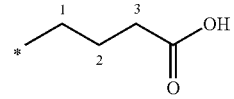 is used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

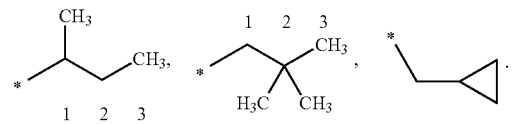

wherein the carboxy group is attached to the third carbon atom of the propyl group. The terms "1-methylpropyl-", "2,2-dimethylpropyl-" or "cyclopropylmethyl-" group represent the following groups:

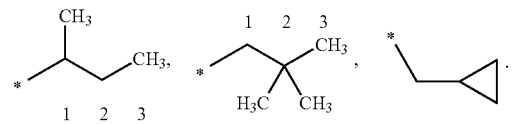

In a definition of a group or substituent the term "oxo" denotes an O-atom which replaces two H-atoms and which is linked to the respective atom via a double bond. A group comprising a —$CH_2$-group may be substituted with an oxo substituent such that the —$CH_2$-group is replaced a —C(=O)-group.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:
The term halogen generally denotes fluorine, chlorine, bromine and iodine.

Alkyl:
The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "alkoxy" means an alkyl moiety attached through an oxygen bridge (i.e., alkyl-O—) and includes groups such as methoxy and ethoxy.

The term "alkylthio" means an alkyl moiety attached through a sulfur bridge (i.e., alkyl-S—) and includes groups such as methylthio and ethylthio.

Alkylene:
The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))-, —(CHCH(CH$_3$)$_2$)— and —C(CH$_3$)(CH$_2$CH$_3$)—.

Alkenyl:
The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=CH$_2$, —CH=CH—CH$_3$, —CH$_2$—CH=CH$_2$.

Alkenylene:
The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —CH=CH—, —CH=CH—CH$_2$—, —CH$_2$—CH=CH—.

Alkynyl:
The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH$_3$, —CH$_2$—C≡CH.

Alkynylene:
The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —C≡C—, —C≡C—CH$_2$—, —CH$_2$—C≡C—.

Carbocyclyl:
The term "carbocyclyl" as used either alone or in combination with another radical, means a mono- or multi-ring ring structure consisting only of carbon containing between one and four rings wherein such rings may be attached together in a pendent manner or may be fused. The term "carbocycle" refers to fully saturated and aromatic ring systems and partially saturated ring systems. The term "carbocycle" additionally encompasses spiro systems, and bridged systems.

Cycloalkyl:
The term "$C_{3-n}$-cycloalkyl", wherein n is an integer 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Cycloalkenyl:
The term "$C_{3-n}$-cycloalkenyl", wherein n is an integer 3 to n, either alone or in combination with another radical, denotes an cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

"ArylC$_{1-6}$alkyl" means a C$_{1-6}$alkyl having at least one alkyl hydrogen atom replaced with an aryl moiety, such as —CH$_2$-phenyl, —CH$_2$—CH$_2$-phenyl and the like.

Heteroaryl:

"Heteroaryl" means an aromatic heterocycle ring of 5- to 10-members and having at least one heteroatom selected from N, O, S, including —C(=O)—, —S(=O)— and —S(=O)$_2$—, and containing at least 1 carbon atom, including both mono- and bicyclic ring systems, and wherein the N and S heteroatom may be optionally oxidized, and the N heteroatom may be optionally quaternized. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, oxadiazolyl, thiadiazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

Heterocycle

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from N, O, S, including —C(=O)—, —S(=O)— and —S(=O)$_2$—, and wherein the N and S heteroatoms may be optionally oxidized, and the N heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

In addition, prodrugs are also included within the context of this invention. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or acid groups are bonded to any group that, when administered to a patient, cleaves to form the hydroxy, amine or acid groups. Thus, representative examples of prodrugs include (but are not limited to) acetate, formate and benzoate derivatives of alcohol and amine functional groups of the compounds of structure (I). Further, in the case of a carboxylic acid (—COOH), esters may be employed, such as methyl esters, ethyl esters, and the like.

With regard to stereoisomers, the compounds of structure (I) may have chiral centers and may occur as racemates, racemic mixtures and as individual enantiomers or diastereomers. All such isomeric forms are included within the present invention, including mixtures thereof.

The compounds of the present invention may exist in a continuum of solid states ranging from fully amorphous to fully crystalline. Furthermore, some of the crystalline forms of the compounds of structure (I) may exist as polymorphs, which are included in the present invention. In addition, some of the compounds of structure (I) may also form solvates with water or other organic solvents. The term solvate is used herein to describe a molecular complex comprising a compound of the present invention and one or more pharmaceutically acceptable solvent molecules. Such solvates are similarly included within the scope of this invention.

The present invention also includes all pharmaceutically acceptable isotopically labeled compounds of structure (I) where on or more atoms are replaced by atoms having the same atomic number but a different atomic mass. Examples include $^2$H and $^3$H for hydrogen, $^{11}$C, $^{13}$C and $^{14}$C for carbon, $^{36}$Cl for chlorine, $^{18}$F for fluorine, $^{123}$I and $^{125}$I for iodine, $^{13}$N and $^{15}$N for nitrogen, and $^{35}$S for sulfur.

Compounds of the present invention include compounds of structure (I) as defined, including all polymorphs, prodrugs, isomers (including optical, geometric and tautomeric), salts, solvates and isotopes thereof.

In an embodiment, GPR119 agonists of the present invention may be used to treat subjects with a variety of diseases and conditions.

In an embodiment, GPR119 agonists of the present invention may be used to treat diseases and conditions which are mediated by the modulating the activity of GPR119.

In an embodiment, GPR119 agonists of the present invention may be used to treat diabetes, in particular type 2 diabetes mellitus or type 1 diabetes mellitus.

In an embodiment, GPR119 agonists of the present invention may be used to treat obesity.

In another embodiment GPR119 agonists of the present invention may be used to treat type 1 diabetes, type 2 diabetes, insufficient glycemic control, insulin resistance, hyperglycemia, hyperlipidemia, hypercholesterinemia, dyslipidemia, syndrome X, metabolic syndrom, obesity, hypertension, chronic systemic inflammation, retinopahtie, neuropathie, nephropathie, atherosclerosis, endothelial dysfunction and bone related conditions such as osteoporosis, rheumatoid arthritis or osteoarthritis.

In another embodiment GPR119 agonists of the present invention may be used to treat, slow, delay or reverse a progression of impaired glucose tolerance, impaired fasting blood, glucose insulin resistance and/or metabolic syndrom to type 2 diabetes.

In another embodiment GPR119 agonists of the present invention may be used to treat or improve the glycemic control and/or to reduce fasting blood glucose, postprandial glucose and/or of glycosylated hemoglobin HbA1c.

In another embodiment GPR119 agonists of the present invention may be used to prevent, slow progression of, delay or treat of a condition or disorder selected from the group consisting of complications of diabetes mellitus, for example cataracts and micro- and macrovascular diseases, such as nephropathy, retinopathy, neuropathy, tissue ischaemia, diabetic foot, arteriosclerosis, myocardial infarction, acute coronary syndrome, unstable angina pectoris, stable angina pectoris, stroke, peripheral arterial occlusive disease, cardiomyopathy, heart failure, heart rhythm disorders and vascular restenosis.

In another embodiment GPR119 agonists of the present invention may be used to reduce body weight and/or body fat, or prevent an increase in body weight and/or body fat, or to facilitate a reduction in body weight and/or body fat In another embodiment GPR119 agonists of the present invention may be used to prevent, slow, delay or treat the degeneration of pancreatic beta cells and/or the decline of the functionality of pancreatic beta cells and/or to improve and/or restore the functionality of pancreatic beta cells and/or restore the functionality of pancreatic insulin secretion In another embodiment GPR119 agonists of the present invention may be used to maintain and/or improve the insulin sensitivity and/or to treat or prevent hyperinsulinemia and/or insulin resistance In addition, the compounds of the present invention may be useful in combination with one or more additional therapeutic agents, particularly therapeutic agents suitable for the treatment and/or prevention of the conditions and diseases presented previously. Additional therapeutic agents which may be suitable for combination with one or more compounds of the present invention which include insulin and insulin analogs, sulfonylureas (such as glibenclamide, glimepiride, tolbutamide), meglitinides (such as nateglinide, mitiglinide), biguanides (especially metformin), PPAR modulators including the thiazolidinediones (such as pioglitazone, rivoglitazone), DPP-4 inhibitors (such as alogliptin, linagliptin), alpha-glucosidase inhibitors (such as acarbose, miglitol, voglibose), GLP-1 analogs (such as exenitide, liraglutide), SGLT-2 inhibitors (such as dapagliflozin, remogliflozin, sergliflozin), amylin analogs (such as pramlintide) and incretin mimetics.

In another embodiment of the invention, pharmaceutical compositions comprising one or more GPR119 receptor agonists are disclosed. For the purposes of administration, the compounds of the present invention may be formulated as pharmaceutical compositions. Pharmaceutical compositions of the present invention comprise a GPR119 receptor agonist of the present invention and a pharmaceutically acceptable carrier and/or diluent. The GPR119 receptor agonist is present in the composition in an amount which is effective to treat a particular disorder—that is, in an amount sufficient to achieve GPR119 receptor agonist activity, and preferably with acceptable toxicity to the patient. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a GPR119 receptor agonist, diluents, dispersing and surface active agents, binders, and lubricants. One skilled in this art may further formulate the GPR119 receptor agonist in an appropriate manner, and in accordance with accepted practices, such as those disclosed in *Remington's Pharmaceutical Sciences*, Gennaro, Ed., Mack Publishing Co., Easton, Pa. 1990.

In another embodiment, the present invention provides a method for treating various diseases and/or conditions as described hereinbefore and hereinafter, in particular obesity and diabetes and related conditions as discussed above. Such methods include administering of a compound of the present invention to a patient in an amount sufficient to treat the condition. In this context, "treat" includes prophylactic administration. Such methods include systemic administration of a GPR119 receptor agonist of this invention, preferably in the form of a pharmaceutical composition as discussed above. As used herein, systemic administration includes oral and parenteral methods of administration.

The dose range of the compounds of general formula (I) applicable per day is usually from 0.001 to 10 mg, preferably from 0.01 to 8 mg per kg body weight of the patient. Each dosage unit may conveniently contain from 0.1 to 1000 mg of a compound according to the invention.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

For oral administration, suitable pharmaceutical compositions of GPR119 receptor agonists include powders, granules, pills, tablets, lozenges, chews, gels, and capsules as well as liquids, syrups, suspensions, elixirs, and emulsions. The compounds of the invention may also be used in fast dissolving, fast disintegrating dosage forms. These compositions may also include anti-oxidants, flavorants, preservatives, suspending, thickening and emulsifying agents, colorants, flavoring agents and other pharmaceutically acceptable additives. Formulations for oral administration may be formulated to be immediate release or modified release, where modified release includes delayed, sustained, pulsed, controlled, targeted and programmed release.

For parenteral administration, the compounds of the present invention are administered directly into the blood stream, into muscle, or into an internal organ via an intravenous, intraarterial, intraperitoneal, intramuscular, subcutaneous or other injection or infusion. Parenteral formulations may be prepared in aqueous injection solutions which may contain, in addition to the GPR119 receptor agonist, buffers, antioxidants, bacteriostats, salts, carbohydrates, and other additives commonly employed in such solutions. Parenteral administrations may be immediate release or modified release (such as an injected or implanted depot).

Compounds of the present invention may also be administered topically, (intra)dermally, or transdermally to the skin or mucosa. Typical formulations include gels, hydrogels, lotions, solutions, creams, ointments, dressings, foams, skin patches, wafers, implants and microemulsions. Compounds of the present invention may also be administered via inhalation or intanasal administration, such as with a dry powder, an aerosol spray or as drops. Additional routes of administration for compounds of the present invention include intravaginal and rectal (by means of a suppository, pessary or enema), and ocular and aural.

The following examples are provided for purposes of illustration, not limitation. In summary, the GPR119 receptor agonists of this invention may be synthesized and assayed by the general methods disclosed in the following Examples.

EXAMPLES

HPLC Methods for Analyzing the Samples
Retention Time, $t_R$, in Minutes
Analytical HPLC-MS Method 1
  Platform: Agilent 1100 series: equipped with an auto-sampler, an UV detector (220 nM and 254 nM), a MS detector (APCI);

HPLC column: Phenomenex Synergi: MAX-RP, 2.0×50 mm column;
HPLC gradient: 1.0 mL/minute, from 10% acetonitrile in water to 90% acetonitrile in water in 2.5 minutes, maintaining 90% for 1 minute. Both acetonitrile and water have 0.025% TFA.

Analytical HPLC-MS Method 2
Platform: Agilent 1100 series: equipped with an auto-sampler, an UV detector (220 nM and 254 nM), a MS detector (APCI);
HPLC column: Phenomenex Synergi-Max RP, 2.0×50 mm column;
HPLC gradient: 1.0 mL/minute, from 5% acetonitrile in water to 95% acetonitrile in water in 13.5 minutes, maintaining 95% for 2 minute. Both acetonitrile and water have 0.025% TFA.

Analytical HPLC-MS Method 3
Platform: Agilent 1100 series: equipped with an auto-sampler, an UV detector (220 nM and 254 nM), a MS detector (electrospray);
HPLC column: XTerra MS, $C_{18}$, 5µ, 3.0×250 mm column;
HPLC gradient: 1.0 mL/minute, from 10% acetonitrile in water to 90% acetonitrile in water in 46 minutes, jump to 99% acetonitrile and maintain 99% acetonitrile for 8.04 minutes. Both acetonitrile and water have 0.025% TFA.

Analytical HPLC-MS Method 4
Platform: Agilent 1100 series: equipped with an auto-sampler, an UV detector (220 nM and 254 nM), a MS detector (electrospray);
HPLC column: Waters XBridge 5µ C18 110A, 3.0×100 mm
HPLC gradient: 1.5 mL/min, from 5% acetonitrile in water to 90% acetonitrile in water in 9.86 minutes, from 90% acetonitrile in water to 95% acetonitrile in water in 0.1 minutes, hold at 95% for 1.19 minutes. Both acetonitrile and water have 0.04% $NH_4OH$ Analytical HPLC-MS Method 5
Platform: Gilson 215 Auto-sampler, Dionex Thermostatted Column Compartment TCC-100 held at 30° C., Dionex PDA-100 Photodiode Array Detector (220 nm and 254 nm), Dionex P680 HPLC pump, Thermo Finnigan MSQ single quad Mass Spectrometer (APCI)
HPLC column: Phenomenex Gemini 5µ C18 110A, 3.0×150 mm
HPLC gradient: 1.5 mL/min, from 5% acetonitrile in water to 90% acetonitrile in water in 9.86 minutes, from 90% acetonitrile in water to 95% acetonitrile in water in 0.1 minutes, hold at 95% for 1.19 minutes. Both acetonitrile and water have 0.04% $NH_4OH$ Analytical HPLC-MS Method 6
Platform: Agilent 1100 series: equipped with an auto-sampler, an UV detector (220 nM and 254 nM), a MS detector (APCI);
HPLC column: Phenomenex Synergi-Max RP, 2.0×50 mm column;
HPLC gradient: from 5% B to 95% B in A in 6.43 minutes, 9.17 minutes total run time. A=10 mM $NH_4OH$ in water, B=75% MeOH 25% AcN Preparative HPLC-MS
Platform: Shimadzu HPLC equipped with a Gilson 215 auto-sampler/fraction collector, UV detector and a PE Sciex API150EX mass detector;
HPLC column: BHK ODS-O/B, 5µ, 30×75 mm
HPLC gradient: 35 mL/minute, 10% acetonitrile in water to 100% acetonitrile in 7 minutes, maintaining 100% acetonitrile for 3 minutes, with 0.025% TFA.

Chiral HPLC
Platform: Dionex P680A and P680P pumps, Dionex PAD 100 photodiode array detector, Jasco CD 2095 plus chiral detector, Gilson 215 liquid handler. Analytical Columns are 0.46×25 cm, 5 µm; preparative columns are 2×25 cm, 5 µm.

DCM—dichloromethane
TFA—trifluoroacetic acid
DMA—N,N-dimethylacetamide

Example 1

2,3-Dihydro-1H-pyrrolo[3,2-b]pyridine

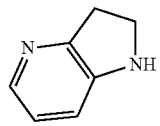

1-1

Step 1A: 2,3-Dihydro-1H-pyrrolo[3,2-b]pyridine (1-1)
To a solution of 1H-pyrrolo[3,2-b]pyridine (1.18 g, 10 mmol) in 100 mL of THF, was added borane tetrahydrofuran complex (60 mL of a 1 M solution, 6 eq) and the mixture was heated at reflux for 5 h. After allowing the reaction to cool down to room temperature, water was added slowly and the solution was extracted with ethyl acetate twice. The combined extracts were washed with a saturated solution of sodium bicarbonate, dried over sodium sulfate and evaporated. The residue was purified on silica gel (eluent: 15% methanol in DCM) to give 0.17 g of 2,3-dihydro-1H-pyrrolo [3,2-b]pyridine 1-1.

Example 2

4-[6-(2,3-Dihydro-pyrrolo[3,2-b]pyridin-1-yl)-pyrimidin-4-yloxy]-piperidine-1-carboxylic acid isopropyl ester

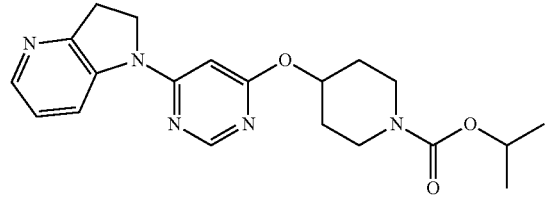

2-1

Step 2A: 4-Hydroxy-piperidine-1-carboxylic acid isopropyl ester (2a)
To a solution of 4-hydroxyl-piperidine (8.1 g, 80 mmol) and triethylamine (11.2 mL, 1 eq) in 200 mL of DCM, was added isopropyl chloroformate (80 mL of a 1 M solution in toluene, 1 eq). The reaction mixture was stirred at room temperature for 3 h, quenched with a saturated solution of bicarbonate and extracted with DCM twice. The combined extracts were washed with a saturated solution of bicarbonate, dried over magnesium sulfate and evaporated to give 2a.
Step 2B: 4-(6-Chloro-pyrimidin-4-yloxy)-piperidine-1-carboxylic acid isopropyl ester (2b)

To a solution of 2a (0.76 g, 4.06 mmol) in 10 mL of THF at room temperature, was added potassium tert-butoxide (0.65 g, 1.4 eq). The resulting mixture was stirred at room temperature for 30 minutes then 4,6-dichloropyrimidine (0.8 g, 1.3 eq) was added. The reaction mixture was stirred at room temperature for 16 h then the solvent was removed under a stream of nitrogen. The residue was taken up with DCM and purified by flash chromatography (elution with 0-40% ethyl acetate and 0.1% TEA in hexanes) to give 0.51 g of 2b (42% yield).

Step 2C: 4-[6-(2,3-Dihydro-pyrrolo[3,2-b]pyridin-1-yl)-pyrimidin-4-yloxy]-piperidine-1-carboxylic acid isopropyl ester (2-1)

A mixture of 2b (100 mg, 0.33 mmol), potassium tert-butoxide (0.1 g, 2.7 eq), 1-1 (0.35 mmol, 1.05 eq), tris(dibenzylideneacetone)dipalladium (32 mg, 0.1 eq), tri-t-butylphosphonium tetrafluoroborate (40 mg, 0.4 eq) and dioxane (1 mL) was heated at 80° C. for 18 h in a sealed vial. After allowing the reaction to cool down to room temperature, THF was added and the mixture was filtered. The filtrate was concentrated under a stream of nitrogen and the residue was taken up with 1 mL of THF and purified by preparative HPLC to afford 2-1.

The following compounds were made according to this procedure

| No. | R | MH+ | MW | Retention Time (Min) | HPLC Gradient |
|---|---|---|---|---|---|
| 2-1 | (pyrrolopyridine) | 384.4 | 383.4 | 5.22 | Method 5 |
| 2-2 | (indoline) | 383.4 | 382.4 | 6.47 | Method 4 |
| 2-3 | (5-F-indoline) | 401.4 | 400.4 | 6.51 | Method 4 |
| 2-4 | (5-NO2-indoline) | 428.3 | 427.4 | 6.32 | Method 4 |

Example 3

4-[6-(5-Bromo-2,3-dihydro-indol-1-yl)-pyrimidin-4-yloxy]-piperidine-1-carboxylic acid tert-butyl ester 3-1

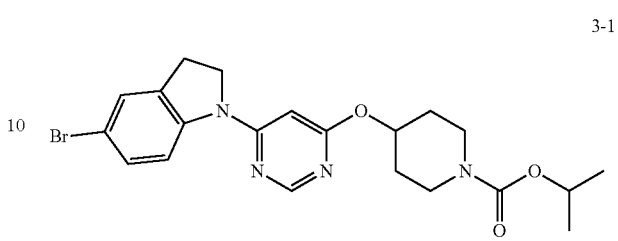

Step 3A: 4-(6-Chloro-pyrimidin-4-yloxy)-piperidine-1-carboxylic acid tert-butyl ester (3a)

To a solution of 4-hydroxy-piperidine-1-carboxylic acid tert-butyl ester (3.1 g, 15.5 mmol) and potassium tert-butoxide (1.74 g, 1 eq) in 20 mL THF at 0° C., was added 4,6-dichloropyrimidine (2.3 g, 1 eq). The reaction mixture was stirred for 1 h then a solution of saturated sodium bicarbonate was added. The aqueous layer was extracted with ethyl acetate twice and the combined extracts were washed with a solution of saturated sodium bicarbonate, dried over magnesium sulfate and evaporated. The residue was purified on silica gel (eluent: 20% ethyl acetate in hexane) to give 2.49 g (51% yield) of 3a.

Step 3B: 4-[6-(5-Bromo-2,3-dihydro-indol-1-yl)-pyrimidin-4-yloxy]-piperidine-1-carboxylic acid tert-butyl ester (3b)

5-Bromoindoline (60 mg, 0.3 mmol) and potassium tert-butoxide (0.1 g, 3 eq) were stirred for 5 minutes in dioxane (1 mL). 3a (0.1 g, 1.05 eq) was added and the mixture was stirred at 80° C. for 72 h. The solvent was removed under vacuum and the residue was dissolved in THF and purified by preparative HPLC to give 3b.

Step 3C: 4 4-[6-(5-Bromo-2,3-dihydro-indol-1-yl)-pyrimidin-4-yloxy]-piperidine-1-carboxylic acid tert-butyl ester (3-1)

3b was taken up with DCM (10 mL) and TFA was added (3 mL). The mixture was stirred at room temperature for 3 h then concentrated under a stream of nitrogen. The residue (32 mg, 0.065 mmol) was taken up with DCM (1 mL) and triethylamine was added (0.2 mL, 22 eq). Diisopropyl chloroformate (0.1 mL of a 1 M solution, 1.5 eq) was added and the mixture was stirred at room temperature for 3 h. The solvent was removed under a stream of nitrogen and the residue was purified by preparative HPLC to give 3-1, LCMS 463.3 (MH+), $t_R$=7.18 (Method 4).

Example 4

4-[6-(5-Methanesulfonyl-2,3-dihydro-indol-1-yl)-pyrimidin-4-yloxy]-piperidine-1-carboxylic acid isopropyl ester 4-1

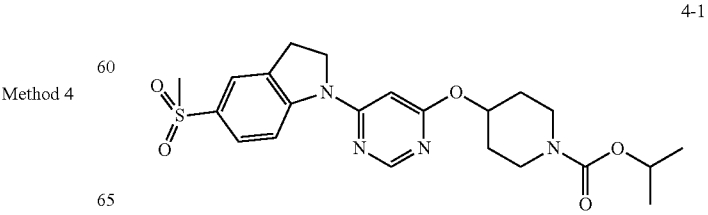

25

Step 4A: 4-[6-(5-Methanesulfonyl-2,3-dihydro-indol-1-yl)-pyrimidin-4-yloxy]-piperidine-1-carboxylic acid tert-butyl ester (4a)

To a suspension of sodium hydride (0.25 g, 2 eq) in 10 mL of DMF, was added 5-methanesulfonyl-2,3-dihydro-1H-indole (0.63 g, 1 eq). The mixture was stirred at room temperature for 10 minutes then 3a (1 g, 3.19 mmol) was added. The resulting mixture was heated up to 80° C. for 18 h. The reaction mixture was then allowed to cool down to room temperature and brine (200 mL) was added. The solution was extracted with DCM twice (200 mL then 50 mL). The combined extracts were washed with brine (2×50 mL), dried over magnesium sulfate and filtered. The solvent was removed under vacuum to give an oil which was purified by column chromatography (elution with 10-100% ethyl acetate and 0.1% TEA in hexanes) to give 0.61 g of 4a (40% yield), LCMS 475.2 (MH+).

Step 4B: 5-Methanesulfonyl-1-[6-(piperidin-4-yloxy)-pyrimidin-4-yl]-2,3-dihydro-1H-indole (4b)

To a solution of 4a (0.55 g) in 8 mL of DCM, was added trifluoroacetic acid (3 mL, 33 eq) at room temperature. The reaction mixture was stirred at room temperature for 3 h then the solvent and excess trifluoroacetic acid were removed under a stream of nitrogen to give 0.57 g of 4b.

Step 4C: 4-[6-(5-Methanesulfonyl-2,3-dihydro-indol-1-yl)-pyrimidin-4-yloxy]-piperidine-1-carboxylic acid isopropyl ester (4-1)

To a solution of 4b (0.12 mmol) and triethylamine (0.2 mL, 12 eq) in 1 mL of DCM, was added the isopropyl chloroformate (1.3 eq). The mixture was stirred at room temperature for 22 h and the solvent volume was reduced to 0.7 mL under a stream of nitrogen. The residue was purified by preparative HPLC to afford 4-1, LCMS 461.2 (MH+).

The following compounds were made according to this procedure using the corresponding electrophile in the last step

| No. | R$^1$ | MH+ | MW | Retention Time (Min) | HPLC Gradient | EC50 (nM) |
|---|---|---|---|---|---|---|
| 4-1 | —C(O)OCH(CH$_3$)$_2$ | 461.2 | 460.55 | 4.60 | Method 6 | 33 |
| 4-2 | —C(O)OCH$_2$CH(CH$_3$)$_2$ | 475.4 | 474.6 | 5.67 | Method 4 | 42 |
| 4-3 | —CH$_2$(O)OC(CH$_3$)$_3$ | 489.4 | 488.6 | 5.37 | Method 4 | 168 |

Example 5

4-[6-(5-Methanesulfonyl-2,3-dihydro-indol-1-yl)-pyrimidin-4-yloxy]-piperidine-1-carboxylic acid cyclobutyl ester

5-1

26

Step 5A: 4-[6-(5-Methanesulfonyl-2,3-dihydro-indol-1-yl)-pyrimidin-4-yloxy]-piperidine-1-carboxylic acid cyclobutyl ester (5-1)

To a solution of the cyclobutanol (0.48 mmol, 4 eq) and triethylamine (0.3 mL, 4.4 eq) in 1 mL of DCM, was added 4-nitrophenyl chloroformate (0.1 g, 4.2 eq) and the mixture was stirred at room temp for 17 h. This solution was then added to a vial containing 4b (0.12 mmol) and the reaction mixture was stirred for 5 h at room temperature. The solvent volume was reduced to 0.7 mL under a stream of nitrogen and the residue was purified by preparative HPLC to afford 5-1, LCMS 473.4 (MH+).

The following compounds were made according to this procedure using the corresponding starting alcohol.

| No. | R$^6$ | MH+ | MW | Retention Time (Min) | HPLC Gradient | EC50 (nM) |
|---|---|---|---|---|---|---|
| 5-1 | cyclobutyl | 473.4 | 472.6 | 5.46 | Method 4 | 24 |
| 5-2 | cyclopropylmethyl | 473.2 | 472.5 | 5.46 | Method 5 | 23 |
| 5-3 | sec-butyl | 475.4 | 474.6 | 5.65 | Method 4 | 35 |
| 5-4 | 2-methoxy-1-methyl-ethyl | 490.8 | 490.6 | 4.91 | Method 4 | 100 |
| 5-5 | 2-fluoro-1-fluoromethyl-ethyl | 497.1 | 496.5 | 6.57 | Method 2 | 242 |

Example 6

4-[6-(5-Methanesulfonyl-2,3-dihydro-indol-1-yl)-pyrimidin-4-ylamino]-piperidine-1-carboxylic acid isopropyl ester

6-1

Step 6A: 1-(6-Chloro-pyrimidin-4-yl)-5-methanesulfonyl-2,3-dihydro-1H-indole (6a)

To a suspension of sodium hydride (0.24 g, 1.5 eq) in 10 mL of DMF at 0° C., was added 5-methanesulfonyl-2,3-dihydro-1H-indole (0.8 g, 4.05 mmol). The mixture was stirred at 0° C. for 10 minutes, then 4,6-pyrimidine dichloride (0.8 g, 1 eq) was added. The resulting mixture was stirred at room temperature for 4 h. The reaction mixture was then quenched with brine (100 mL) and extracted with ethyl acetate (100 mL then 3×50 mL). The combined extracts were washed with brine, dried over magnesium sulfate and filtered. The solvent was removed under vacuum and the crude product was purified by 3 consecutive column chromatography (elution with 25-100% ethyl acetate and 0.1% TEA in hexanes) to give 0.51 g of 6a (41% yield).

Step 6B: 4-[6-(5-Methanesulfonyl-2,3-dihydro-indol-1-yl)-pyrimidin-4-ylamino]-piperidine-1-carboxylic acid tert-butyl ester (6b)

A mixture of 6a (0.4 g, 1.29 mmol), 4-amino-piperidine-1-carboxylic acid tert-butyl ester (0.4 g, 1.5 eq), DMA (5 mL) and potassium carbonate (0.4 g, 2.2 eq) was heated at 80° C. for 42 h. After allowing the reaction mixture to cool down to room temperature, 100 mL of brine was added and the mixture was extracted with ethyl acetate twice (100 mL and 30 mL). The combined extracts were washed with brine (2×50 mL), dried over magnesium sulfate and filtered. The solvent was removed under vacuum to give a solution of 6b in DMA.

Step 6C: [6-(5-Methanesulfonyl-2,3-dihydro-indol-1-yl)-pyrimidin-4-yl]-piperidin-4-yl-amine (6c)

The solution of 6b obtained above was diluted with 5 mL of DCM and trifluoroacetic acid (5 mL, 60 eq) was added. The reaction mixture was stirred at room temperature for 2 h then concentrated under a stream of nitrogen overnight and purified on preparative HPLC to afford 104 mg (17%) of 6c.

Step 6D: 4-[6-(5-Methanesulfonyl-2,3-dihydro-indol-1-yl)-pyrimidin-4-ylamino]-piperidine-1-carboxylic acid isopropyl ester (6-1)

To a solution of 6c (104 mg, 0.21 mmol) and triethylamine (0.1 mL, 3.3 eq) in 1 mL of DCM, was added isopropyl chloroformate (0.24 mL, 1.1 eq). The mixture was stirred at room temperature for 2 h. The crude mixture was poured onto silica and eluted with ethyl acetate/hexane then chromatographed over a silica gel column (elution with 25-100% ethyl acetate and 0.1% TEA in hexanes) and finally purified on preparative HPLC to give 6-1, LC-MS 460.4 (MH+), $t_R$=4.50 (Method 4). EC50: 611 nM.

Example 7

4-[6-(5-Methanesulfonyl-2,3-dihydro-indol-1-yl)-pyrimidin-4-yl-methylamino]-piperidine-1-carboxylic acid isopropyl ester 7-1

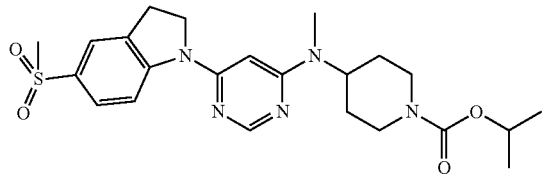

Step 7A: (1-Benzyl-piperidin-4-yl)-carbamic acid tert-butyl ester (7a)

To a solution of 1-Benzyl-piperidin-4-ylamine (0.5 mL, 2.6 mmol) and triethylamine (0.5 mL, 1.3 eq) in 10 mL of DCM, was added di-tert-butyl dicarbonate (0.6 g, 1.04 eq). The mixture was stirred at room temperature for 16 h. It was then diluted with DCM and washed with a solution of saturated bicarbonate (2 mL) and brine (2 mL), dried over magnesium sulfate, filtered and evaporated to give 7a as a solid which was used without further purification on the next step.

Step 7B: (1-Benzyl-piperidin-4-yl)-methyl-amine (7b).

To a suspension of LAH (0.5 g, 5 eq) in THF (10 mL), was added 7a and the mixture was refluxed for 72 h. After allowing the reaction mix to cool down to room temperature, 0.5 mL of water, 1 mL of 1 M sodium hydroxide and 1.5 mL of water were added slowly and sequentially. Ethyl acetate was added and the mixture was filtered. Removal of the solvent gave 0.36 g (66% on both steps) of 7b as an oil which was used without further purification on the next step.

Step 7C: (1-Benzyl-piperidin-4-yl)-[6-(5-methanesulfonyl-2,3-dihydro-indol-1-yl) -pyrimidin-4-yl]-methyl-amine (7c)

A mixture of 7b (0.14 g, 2.1 eq), 6a (0.1 g, 0.3 mmol) and potassium carbonate (0.1 g, 2.2 eq) in 1 mL of DMA was heated up to 90° C. for 48 h then cooled down to room temperature and diluted with DCM (2 mL) and brine (2 mL). The layers were separated and the aqueous extracted with DCM (2×2 mL). The combined extracts were washed with brine (2×50 mL), dried over magnesium sulfate, filtered and evaporated. The residue was diluted with acetonitrile and purified on preparative HPLC to afford 7c.

Step 7D: [6-(5-Methanesulfonyl-2,3-dihydro-indol-1-yl)-pyrimidin-4-yl]-piperidin-4-yl -methyl-amine (7d)

7c was taken up in DCM (2 mL). Diisopropylethylamine (0.6 mL, 11 eq) and 1-chloroethyl chloroformate (0.2 mL, 5.7 eq) were added. The reaction mixture was stirred at room temperature for 22 h. The solvent was then evaporated under a stream of nitrogen and the residue was dissolved in methanol and heated at 50° C. for 3 h. The solvent was removed under a stream of nitrogen and the residue was purified by preparative HPLC to give 25 mg (15%) of 7d.

Step 7E: 4-[6-(5-Methanesulfonyl-2,3-dihydro-indol-1-yl)-pyrimidin-4-yl-methylamino]-piperidine-1-carboxylic acid isopropyl ester (7-1).

7d was dissolved in DCM (1 mL) and triethylamine (0.1 mL, 14 eq) was added. Isopropyl chloroformate (0.1 mL of a 1 M solution in toluene, 2 eq) was added and the reaction mixture was stirred at room temperature for 17 h. The solution was evaporated and purified by preparative HPLC to give 7-1; LC-MS 474.0 (MH+), $t_R$=5.21 (Method 5). EC50: 69 nM.

Example 8

4-[6-(5-Methanesulfonyl-2,3-dihydro-indol-1-yl)-5-methoxy-pyrimidin-4-yloxy]-piperidine-1-carboxylic acid isopropyl ester 8-1

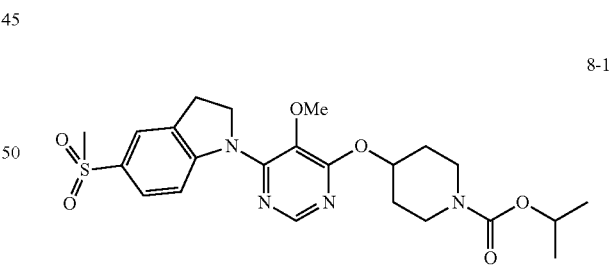

Step 8A: 4-(6-Chloro-5-methoxy-pyrimidin-4-yloxy)-piperidine-1-carboxylic acid isopropyl ester (8a)

To a solution of 2a (3.18 g, 17 mmol) in 18 mL of THF at room temperature, was added potassium tert-butoxide (2.06 g, 1.2 eq). The resulting mixture was stirred at room temperature for 30 minutes then 4,6-dichloro-5,methoxy-pyrimidine (3 g, 17 mmol) was added. The reaction mixture was stirred at room temperature for 8 h then the solvent was evaporated. The residue was taken up with DCM and purified on silica gel (elution with 25% ethyl acetate in hexanes) to give 3.64 g of 8a (65% yield).

Step 8B: 4-[6-(5-Methanesulfonyl-2,3-dihydro-indol-1-yl)-5-methoxy-pyrimidin-4-yloxy]-piperidine-1-carboxylic acid isopropyl ester (8-1)

A mixture of 8a (49 mg, 0.15 mmol), cesium carbonate (0.11 g, 2 eq), 5-Methanesulfonyl-2,3-dihydro-1H-indole (35 mg, 1.2 eq), tris(dibenzylideneacetone)-dipalladium (31 mg, 0.1 eq), tri-t-butylphosphonium tetrafluoroborate (37 mg, 0.8 eq) and dioxane (1.5 mL) was heated at 90° C. for 4 h. The mixture cooled to room temperature, dioxane was added and the mixture was filtered and washed with DCM. The filtrate was concentrated under a stream of nitrogen and the residue was taken up in 1 mL of THF and was purified by preparative HPLC to afford 8-1; LCMS 491.2 (MH+), $t_R$=5.35 (Method 6). EC50: 201 nM.

Example 9

4-[5-Methyl-6-(5-nitro-2,3-dihydro-indol-1-yl)-pyrimidin-4-yloxy]-piperidine-1-carboxylic acid isopropyl ester

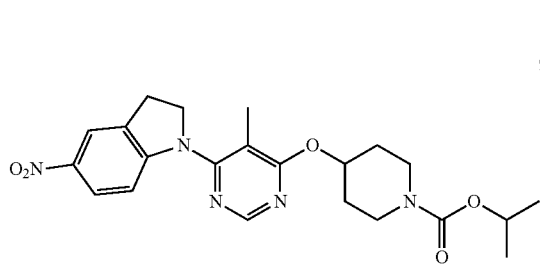

9-1

Step 9A: 4-(6-Chloro-5-methyl-pyrimidin-4-yloxy)-piperidine-1-carboxylic acid tert-butyl ester (9a)

To a solution of 4,6-dichloro-5-methyl-pyrimidine (8.15 g, 50 mmol) in 200 mL of THF, was added 4-hydroxy-piperidine-1-carboxylic acid tert-butyl ester (10 g, 1 eq) and potassium tert-butoxide (6.1 g, 1.2 eq) at 0° C. The resulting mixture was stirred at room temperature for 16 h then quenched with a saturated solution of NH$_4$Cl and extracted with ethyl acetate. The combined organic layers were washed with water and brine, dried over magnesium sulfate and concentrated to give crude 9a.

Step 9B: 4-(6-Chloro-5-methyl-pyrimidin-4-yloxy)-piperidine-1-carboxylic acid isopropyl ester (9b).

9a was dissolved in a 4 M solution of HCl in dioxane (60 mL). The solution was stirred at room temperature for 3 h and the solvent was removed. The residue was taken up in 200 mL of DCM and 40 mL of toluene and cooled to 0° C. Isopropyl chloroformate (60 mL of a 1 M solution in toluene, 1.2 eq) and diisopropylethylamine (24 mL) were added. The mixture was stirred for 36 h, washed with 1 M HCl (3×100 mL), 100 mL of water and 100 mL of brine. The solvent was evaporated and the residue taken up in 50 mL of hexane, cooled at 0° C. and stirred for 2 h to give a precipitate which was filtered and washed with hexane. 2.89 g of 9b were obtained. The filtrate was concentrated and recrystallized with IPA. Some light yellow crystals were obtained, filtered and washed with IPA to give 3.38 g of 9b. The filtrate was concentrated and purified on silica gel (eluent: 20% ethyl acetate in hexane) to give 2.2 g of 9b. Total yield of 9b: 8.47 g (54%).

Step 9C: 4-[5-Methyl-6-(5-nitro-2,3-dihydro-indol-1-yl)-pyrimidin-4-yloxy]-piperidine-1-carboxylic acid isopropyl ester (9-1)

Sodium hydride (16 mg of a 60% suspension in oil, 2 eq) was added to a mixture of 9b (63 mg, 0.2 mmol) and 5-Nitro-2,3-dihydro-1H-indole (41 mg, 1.05 eq) in 1 mL of DMF. The mixture was heated at 90° C. for 2 h. The reaction was cooled down to room temperature and poured into 10 mL of water. The solution was extracted with ethyl acetate 3 times, dried and concentrated. The residue was taken up with methanol and dichloromethane and purified on preparative HPLC to give 9-1.

4-[6-(2,3-Dihydro-pyrrolo[3,2-b]pyridin-1-yl)-5-methyl-pyrimidin-4-yloxy]-piperidine-1-carboxylic acid isopropyl ester 9-2 was made according to the same procedure, LCMS 398.2 (MH+), $t_R$=3.56 (method 2). EC50: 312 nM.

Example 10

4-[2-(5-Methanesulfonyl-2,3-dihydro-indol-1-yl)-pyridin-4-yloxy]-piperidine-1-carboxylic acid isopropyl ester and 4-[4-(5-Methanesulfonyl-2,3-dihydro-indol-1-yl)-pyridin-2-yloxy]-piperidine-1-carboxylic acid isopropyl ester

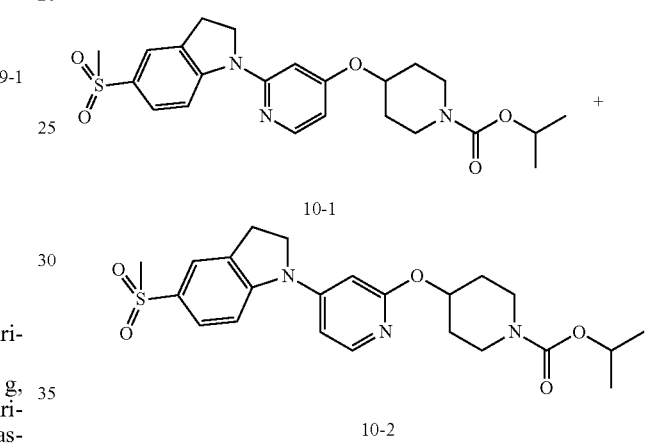

10-1

10-2

Step 10A: 4-(2-Chloro-pyridin-4-yloxy)-piperidine-1-carboxylic acid isopropyl ester (10a) and 4-(4-Chloro-pyridin-2-yloxy)-piperidine-1-carboxylic acid isopropyl ester (10b)

2,4-Dichloropyridine (0.52 g, 3.5 mmol) in 2 mL of DMF was added to a suspension of sodium hydride (60% in oil, 0.16 g, 3 eq) and 2a (0.55 g, 3 mmol) in 8 mL of DMF. The mixture was heated at 90° C. The mixture was allowed to cool to room temperature, water was added to quench the excess sodium hydride and the solution was extracted with ethyl acetate twice, washed with a saturated solution of sodium bicarbonate, dried and evaporated. The crude material was purified on silica gel (eluent: 20% then 50% of ethyl acetate in hexane) to give 10a and 10b (0.55 g of the more polar product and 84 mg of the less polar product).

Step 10B: 4-[4-(5-Methanesulfonyl-2,3-dihydro-indol-1-yl)-pyridin-2-yloxy]-piperidine-1-carboxylic acid isopropyl ester (10-2) and 4-[2-(5-Methanesulfonyl-2,3-dihydro-indol-1-yl)-pyridin-2-yloxy]-piperidine-1-carboxylic acid isopropyl ester (10-1)

Each product (10a and 10b) (30 mg, 0.1 mmol) was then separately taken up with DMF and 5-methanesulfonyl-2,3-dihydro-1H-indole was added (20 mg, 1 eq). To this mixture, was added sodium hydride (60% in oil, 6 mg, 1.5 eq) and the reaction mixture was heated at 90° C. for 1 h. At room temperature, the reaction mixture was then quenched with water and partitioned between ethyl acetate and water. The organic layer was separated, dried over sodium sulfate, filtered and evaporated to dryness. The crude products (10-1 and 10-2) were purified by preparative HPLC, LCMS 460.1 (MH+).

$t_R$=4.72 (Method 2), EC50: 588 nM for 10-1 and LCMS 460.2 (MH+). $t_R$=5.21 (Method 6) for 10-1.

Example 11

4-[4-(5-Methanesulfonyl-2,3-dihydro-indol-1-yl)-[1,3,5]triazin-2-yloxy]-piperidine-1-carboxylic acid tert-butyl ester

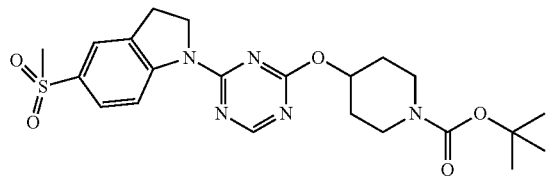

11-1

Step 11A: 1-(4-Chloro-[1,3,5]-triazin-2-yl)-5-methanesulfonyl-2,3-dihydro-1H-indole (11a)

5-Methanesulfonyl-2,3-dihydro-1H-indole (79 mg, 0.4 mmol) was dissolved in dioxane (2 mL). 2,4-Dichloro-[1,3,5]-triazine (60 mg, 1 eq), palladium acetate (11 mg, 5% molar), (+/−)binap (15 mg, 8% molar) and cesium carbonate (131 mg, 1 eq) were added and the reaction mixture was heated at 100° C. for 4 h. The mixture was cooled to room temperature and water was added. The mixture was filtered through celite and washed three times with dioxane. The collected filtrate was evaporated to dryness to give 11a (104 mg) which was used for the next step without further purification.

Step 11B: 4-[4-(5-Methanesulfonyl-2,3-dihydro-indol-1-yl)-[1,3,5]-triazin-2-yloxy]-piperidine-1-carboxylic acid tert-butyl ester (11-1)

11a was dissolved in THF. 4-Hydroxy-piperidine-1-carboxylic acid tert-butyl ester (40 mg, 1 eq) and potassium tert-butoxide (22 mg, 1 eq) were added and the mixture was stirred at room temperature for 3 h, then was quenched with water. The mixture was extracted with ethyl acetate twice, and the organic layer was washed with water and dried over sodium sulfate. The solvent was evaporated and the residue taken up in methanol and dichloromethane and purified by preparative HPLC to give 11-1, LCMS 476.2 (MH+), $t_R$=3.68 (Method 6).

Example 12

4-[2-(5-Methanesulfonyl-2,3-dihydro-indol-1-yl)-pyrimidin-4-yloxy]-piperidine-1-carboxylic acid isopropyl ester and 4-[4-(5-Methanesulfonyl-2,3-dihydro-indol-1-yl)-pyrimidin-2-yloxy]-piperidine-1-carboxylic acid isopropyl ester

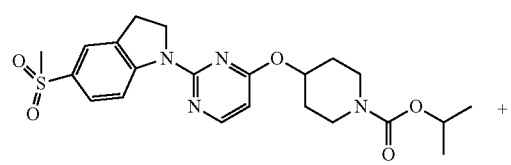

12-1

-continued

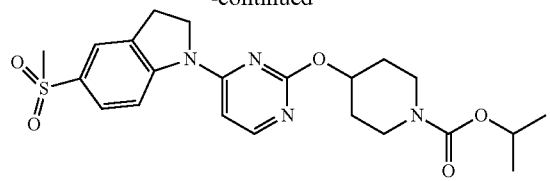

12-2

Step 12A: 4-(2-Chloro-pyrimidin-4-yloxy)-piperidine-1-carboxylic acid isopropyl ester (12a) and 4-(4-Chloro-pyrimidin-2-yloxy)-piperidine-1-carboxylic acid isopropyl ester (12b)

2,4-Dichloro-pyrimidine (2.3 g) was added at 0° C. to a solution of 2a (3.1 g, 1 eq) and potassium tert-butoxide (1.74 g, 1 eq) in 20 mL of THF. The mixture was stirred for 1 h then quenched with water. The product was extracted with ethyl acetate twice, washed with water and dried over sodium sulfate. The solvent was evaporated and the residue was taken up with methanol and dichloromethane and purified on silica gel (eluent: 20% ethyl acetate in hexane) to give a mixture of 12a and 12b. This was used directly on the next step.

Step 12B: 4-[2-(5-Methanesulfonyl-2,3-dihydro-indol-1-yl)-pyrimidin-4-yloxy]-piperidine-1-carboxylic acid isopropyl ester (12-1) and 4-[4-(5-Methanesulfonyl-2,3-dihydro-indol-1-yl)-pyrimidin-2-yloxy]-piperidine-1-carboxylic acid isopropyl ester (12-2

0.19 g (0.6 mmol) of the mixture of 12a and 12b was dissolved in dioxane (3 mL) along with 5-methanesulfonyl-2,3-dihydro-1H-indole (0.12 g, 1 eq), cesium carbonate (0.19 g, 1 eq), palladium acetate (16 mg, 3% molar) and (+/−)-binap (22 mg, 6% molar). The mixture was heated at 100° C. for 4 h, cooled to room temperature, filtered through celite and washed with DCM. The organic layer was collected and evaporated to dryness. The residue was dissolved in methanol and DCM and purified by preparative HPLC to give 12-1 and 12-2; LCMS 475.2 (MH+), $t_R$=4.58 (Method 6) for 12-1 and LCMS 475.2 (MH+), $t_R$=5.55 (Method 6) for 12-2.

Example 13

4-[5-Fluoro-6-(5-methanesulfonyl-2,3-dihydro-indol-1-yl)-pyrimidin-4-yloxy]-piperidine-1-carboxylic acid tert-butyl ester

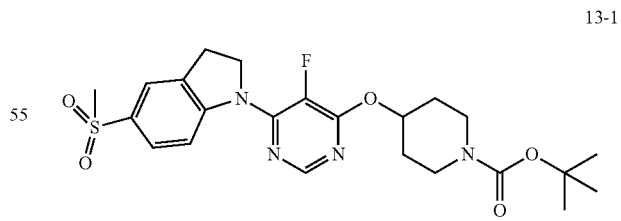

13-1

Step 13A: 4-[5-Fluoro-6-(5-methanesulfonyl-2,3-dihydro-indol-1-yl)-pyrimidin-4-yloxy]-piperidine-1-carboxylic acid tert-butyl ester (13-1)

4a (43 mg, 0.09 mmol) was dissolved in 1 mL of DCE with N-fluorobenzenesulfonimide (62 mg, 0.2 mmol). The mixture was stirred for 2 days at 75° C. then the solvent was evaporated under vacuum. The crude material was dissolved

Example 14

4-[6-(5-Methanesulfonyl-2,3-dihydro-indol-1-yl)-2-methyl-pyrimidin-4-yloxy]-piperidine-1-carboxylic acid isopropyl ester

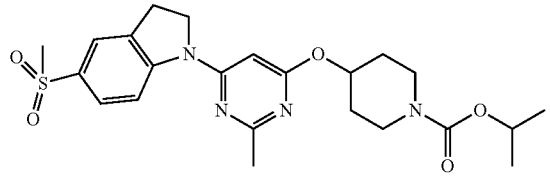

14-1

Step 14A: 4-(6-Chloro-2-methyl-pyrimidin-4-yloxy)-piperidine-1-carboxylic acid isopropyl ester (14a)

4,6-Dichloro-2-methyl-pyrimidine (163 mg, 1 mmol) was dissolved in 4 mL of THF. A solution of tBuOK (112 mg, 1 mmol) and 2a (187 mg, 1 mmol) in 2 mL of THF was added slowly at room temperature. The mixture was stirred at room temperature for 8 h and quenched with a saturated solution of NH₄Cl. The mixture was diluted with water and extracted with DCM. The organic layer was isolated, dried, filtered and evaporated to give 100 mg of 14a.

Step 14B: 4-[6-(5-Methanesulfonyl-2,3-dihydro-indol-1-yl)-2-methyl-pyrimidin-4-yloxy]-piperidine-1-carboxylic acid isopropyl ester (14-1)

14a (100 mg) was dissolved in DMF with 5-methanesulfonyl-2,3-dihydro-1H-indole (0.3 mmol) and NaH (0.3 mmol). The mixture was heated at 90° C. for 4 h. After cooling to room temperature, the mixture was diluted with ethyl acetate and water. The organic layer was washed with a saturated NaHCO₃ solution, isolated, evaporated and purified by preparative HPLC to give 14-1, LCMS 475.1 (MH+).

The following compounds were made according to this procedure using the corresponding dichloropyrimidine in the first step:

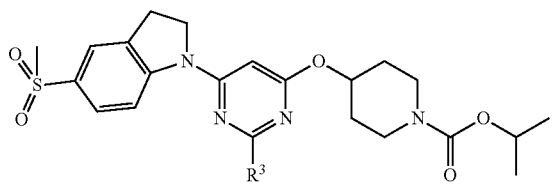

| No. | R³ | MH+ | MW | Retention Time (Min) | HPLC Gradient |
|---|---|---|---|---|---|
| 14-1 | Me | 475.1 | 474.6 | 6.69 | Method 2 |
| 14-2 | SMe | 507.1 | 506.6 | 8.53 | Method 2 |
| 14-3 | Cl | 495.1 | 495.0 | 7.62 | Method 2 |

Example 15

3-[6-(5-Methanesulfonyl-2,3-dihydro-indol-1-yl)-pyrimidin-4-yloxy]-azetidine-1-carboxylic acid tert-butyl ester

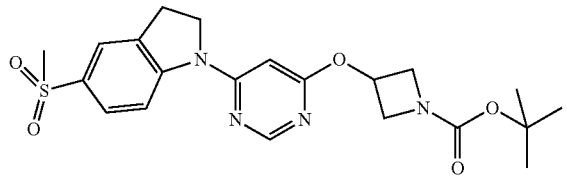

15-1

Step 15A: 3-[6-(5-Methanesulfonyl-2,3-dihydro-indol-1-yl)-pyrimidin-4-yloxy]-azetidine-1-carboxylic acid tert-butyl ester (15-1)

To a suspension of NaH (30 mg, 0.75 mmol) in 1 mL of DMF, was added 3-hydroxy-azetidine-1-carboxylic acid tert-butyl ester (74 mg, 0.43 mmol) and the mixture was stirred at room temperature for 30 minutes. 6a (0.1 g, 0.32 mmol) was added and the mixture was heated at 80° C. for 21 h. The mixture cooled to room temperature and DCM (4 mL) and brine (4 mL) were added. The layers were separated and the aqueous layer was extracted with DCM (3×3 mL). The combined extracts were dried, filtered and evaporated. The residue was purified by preparative HPLC to give 15-1, LCMS 447.1 (MH+), $t_R$=7.27 (method 2). 22% stimulation at 10 µM.

(R)-3-[6-(5-Methanesulfonyl-2,3-dihydro-indol-1-yl)-pyrimidin-4-yloxy]-pyrrolidine-1-carboxylic acid tert-butyl ester 15-2 was also made according to this procedure, LCMS 461.1 (MH+), $t_R$=6.21 (method 2). 26% stimulation at 10 µM.

Example 16

4-{[6-(5-Methanesulfonyl-2,3-dihydro-indol-1-yl)-pyrimidin-4-yl]-methyl-amino}-piperidine-1-carboxylic acid tert-butyl ester

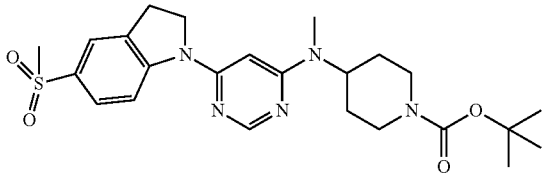

16-1

Step 16A: 4-{[6-(5-Methanesulfonyl-2,3-dihydro-indol-1-yl)-pyrimidin-4-yl]-methyl-amino}-piperidine-1-carboxylic acid tert-butyl ester (16-1)

A mixture of 6b (80 mg, 0.17 mmol), NaH (75 mg, 1.87 mmol) and DMF (1 mL) was stirred at room temperature for 30 minutes. Methyl iodide (0.025 mL, 0.4 mmol) was added and the mixture was heated at 90° C. in a sealed vial for 18 h. After cooling to room temperature, DCM (4 mL) and brine (4 mL) were added. The layers were separated and the aqueous layer was extracted with DCM (3×3 mL). The combined extracts were dried, filtered, evaporated and purified by preparative HPLC to give 16-1, LCMS 488.4 (MH+).

The following compounds were made according to this procedure using the corresponding alkylating agent (NB: NaI (1 eq) was used as an additive to the reaction for the allyl bromide alkylation):

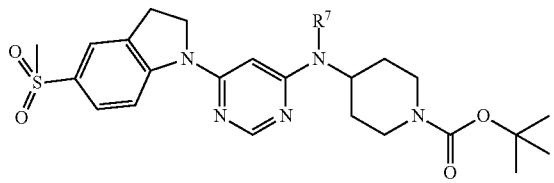

| No. | $R^7$ | MH+ | MW | Retention Time (Min) | HPLC Gradient | EC50 (nM) |
|---|---|---|---|---|---|---|
| 16-1 | methyl | 488.4 | 487.6 | 5.49 | Method 4 | 51 |
| 16-2 | ethyl | 502.4 | 501.6 | 5.77 | Method 4 | 29 |
| 16-3 | methoxymethyl | 518.4 | 517.6 | 5.11 | Method 2 | 906 |
| 16-4 | sec-butyl | 530.4 | 529.7 | 6.46 | Method 4 | 95 |
| 16-5 | allyl | 514.3 | 513.7 | 6.04 | Method 5 | 23 |

Example 17

4-[6-(5-Methanesulfonyl-2,3-dihydro-indol-1-yl)-pyrimidin-4-ylamino]-piperidine-1-carboxylic acid isopropyl ester

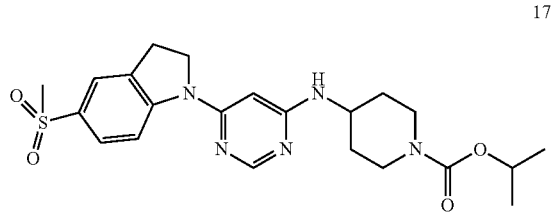

Step 17A: 4-(6-Chloro-pyrimidin-4-ylamino)-piperidine-1-carboxylic acid tert-butyl ester (17a)

To a solution of 4,6-dichloro-pyrimidine (8.9 g, 59.7 mmol) and triethylamine (11 mL, 78.9 mmol) in 90 mL of DCM at 0° C., was added 4-amino-piperidine-1-carboxylic acid tert-butyl ester (4.89 g, 24.4 mmol). The mixture was stirred at room temperature for 3 days, concentrated under vacuum and purified by flash chromatography (eluent: 0 to 50% EtOAc in hexane with 0.1% triethylamine) to afford 3.09 g (40%) of 17a.

Step 17B: 4-[6-(5-Methanesulfonyl-2,3-dihydro-indol-1-yl)-pyrimidin-4-ylamino]-piperidine-1-carboxylic acid tert-butyl ester (17b)

To a solution of NaH (0.62 g, 15.5 mmol, 60% NaH) in 40 mL of DMF, 5-methanesulfonyl-2,3-dihydro-1H-indole (1.9 g, 9.63 mmol) was added and the mixture was stirred at room temperature for 30 minutes. 17a (3.09 g, 9.88 mmol) was added in DMF and the mixture was heated at 85° C. for 17 h. After cooling to room temperature, brine was added (200 mL) and the mixture was extracted with DCM (200 mL then 3×500 mL). The combined extracts were washed with brine (3×100 mL), dried, filtered and evaporated. The residue was purified by flash chromatography (eluent: 25 to 100% EtOAc in hexane with 0.1% triethylamine) to afford 2.83 g (62%) of 17b.

Step 17C: 4-[6-(5-Methanesulfonyl-2,3-dihydro-indol-1-yl)-pyrimidin-4-ylamino]-piperidine-1-carboxylic acid isopropyl ester (17-1).

To a solution of 17b (0.28 g, 0.59 mmol) in 5 mL of DCM, was added TFA (5 mL, 64.9 mmol). The mixture was stirred at room temperature for 2 h then it was evaporated. The residue was dissolved in methanol and bicarbonate resin was added. The mixture was stirred for 1 h, filtered and the solvent was evaporated.

The residue was taken up in THF (5 mL) and triethylamine (0.5 mL, 3.59 mmol). Isopropyl chloroformate (1M in toluene, 0.65 mL, 0.65 mmol) was added and the mixture was stirred at room temperature for 17 h. It was then concentrated and purified by flash chromatography (eluent: 25 to 100% EtOAc in hexane with 0.1% triethylamine) to afford 0.24 g (87%) of 17-1. $t_R$=5.21 (Method 5). EC50: 611 nM.

Example 18

4-[6-(5-Methanesulfonyl-2,3-dihydro-indol-1-yl)-pyrimidin-4-ylamino]-piperidine-1-carboxylic acid isopropyl ester

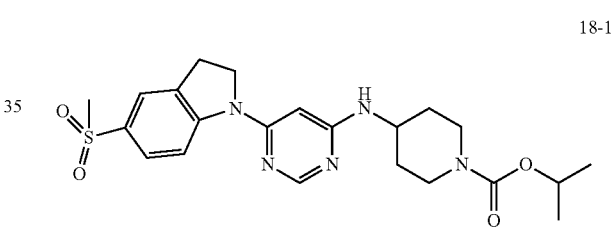

Step 18A: 4-tert-Butoxycarbonylamino-piperidine-1-carboxylic acid isopropyl ester (18a)

To a solution of 4-(N-Boc amino)piperidine (2.61 g, 13 mmol) and triethylamine (3 mL, 21.5 mmol) in 25 mL of DCM, was added isopropyl chloroformate (1 M in toluene, 13.1 mL, 13.1 mmol). The mixture was stirred at room temperature for 20 h. It was then washed with a saturated solution of NaHCO₃ (50 mL), followed by brine (50 mL). The solution was dried, filtered and evaporated to afford 3.26 g (87%) of 18a.

Step 18B: 4-Amino-piperidine-1-carboxylic acid isopropyl ester (18b)

To a solution of 18a (3.26 g, 11.37 mmol) in 10 mL of DCM, was added TFA (5 mL, 64.9 mmol). The mixture was stirred at room temperature for 2 h and the solvent were evaporated. The residue was dissolved in DCM and a saturated solution of NaHCO₃ and 1N NaOH were added until pH was 8. The layers were separated and the aqueous layer was extracted with 3:1 DCM:IPA (3×40 mL). The organic extracts were combined, dried, filtered and evaporated to afford 1.89 g (89%) of 18b.

Step 18C: 4-[6-(5-Methanesulfonyl-2,3-dihydro-indol-1-yl)-pyrimidin-4-ylamino]-piperidine-1-carboxylic acid isopropyl ester (18-1)

A mixture of 18b (1.1 g, 5.9 mmol), 6a (1.5 g, 4.84 mmol) and diisopropylethylamine (3 mL, 18.1 mmol) in 15 mL of DMF was heated at 80° C. for 17 h and at 90° C. for 24 h. The mixture was diluted with 100 mL of DCM, washed with brine (3×50 mL) and the extracts were dried, filtered and concentrated under vacuum. The residue was purified by flash chromatography (elution with 50-100% ethyl acetate and 0.1% TEA in hexanes) and finally purified on preparative HPLC to afford 0.3 g (14%) of 18-1. $t_R$=5.21 (Method 5). EC50: 611 nM.

Example 19

1-[6-(1-Isopropoxycarbonyl-piperidin-4-yloxy)-pyrimidin-4-yl]-2,3-dihydro-1H-indole-5-carboxylic acid

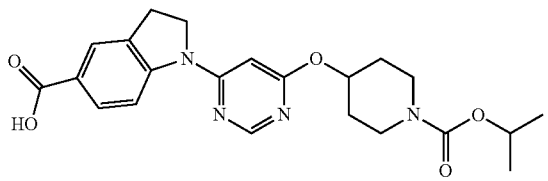

19-1

Step 19A: 2,3-Dihydro-1H-indole-5-carboxylic acid methyl ester (19a)

To a solution of 1H-Indole-5-carboxylic acid methyl ester (1 g, 5.71 mmol) in 10 mL of acetic acid at 0° C., was added sodium cyanoborohydride (1.08 g, 17.18 mmol) over 5 minutes. The mixture was stirred at room temperature for 1 h. Water (3 mL) was added and all the solvents were removed under vacuum. The residue was dissolved in ethyl acetate (150 mL) and saturated NaHCO$_3$ (150 mL). The layers were separated and the aqueous layer was extracted with ethyl acetate (3×75 mL). The combined extracts were washed with brine (150 mL), dried, filtered and evaporated. The residue was purified by flash chromatography (0-50% ethyl acetate in hexane+0.1% triethylamine) to afford 0.99 g (99%) of 19a.

Step 19B: 1-[6-(1-tert-Butoxycarbonyl-piperidin-4-yloxy)-pyrimidin-4-yl]-2,3-dihydro-1H-indole-5-carboxylic acid (19b)

To NaH (0.15 g, 3.75 mmol, 60% dispersion) at 0° C., was added 19a (0.3 g, 0.95 mmol) in 5 mL of DMF. The mixture was stirred at 80° C. for 16 h. The mixture was poured into a separatory funnel and DCM (50 mL), brine (50 mL) and 0.19M HCl (20 mL) were added. The layers were separated and the aqueous layer was extracted with DCM (3×50 mL). The combined extracts were washed with brine (2×50 mL), dried, filtered and evaporated. The residue was purified by preparative HPLC to afford 65 mg (25%) of 19b.

Step 19C: 1-[6-(1-Isopropoxycarbonyl-piperidin-4-yloxy)-pyrimidin-4-yl]-2,3-dihydro-1H-indole-5-carboxylic acid (19c)

To a solution of 19b (65 mg, 0.37 mmol) in 1.5 mL of DCM, was added TFA (1.5 mL, 19.5 mmol) and the reaction was stirred at room temperature for 2 h. The mixture was concentrated to give 19c.

Step 19D: 1-[6-(1-Isopropoxycarbonyl-piperidin-4-yloxy)-pyrimidin-4-yl]-2,3-dihydro-1H-indole-5-carboxylic acid (19-1)

19c was dissolved in 1 mL of THF with 0.5 mL of triethylamine (3.59 mmol). Isopropyl chloroformate (1M in toluene, 2.25 mL, 2.25 mmol) was added and the mixture was stirred at room temperature for 2 h. Water (1 mL) was added followed by NaBH$_4$ (0.5 g, 13.2 mmol) and the mixture was sonicated for 2 minutes and stirred at room temperature for 1 h. THF was removed under vacuum and the aqueous mixture was acidified with 1N HCl, extracted with DCM (3×10 mL) and the combined extracts were washed with brine (10 mL). The solution was dried, filtered and evaporated. The residue was purified by preparative HPLC to afford 19-1 ($t_R$=3.0, Method 5) as well as a small amount of 4-[6-(5-hydroxymethyl-2,3-dihydro-indol-1-yl)-pyrimidin-4-yloxy]-piperidine-1-carboxylic acid isopropyl ester 19-2. $t_R$=5.21 (Method 5).

Example 20

4-[6-(5-Chloro-2,3-dihydro-pyrrolo[3,2-b]pyridin-1-yl)-pyrimidin-4-yloxy]-piperidine-1-carboxylic acid tert-butyl ester

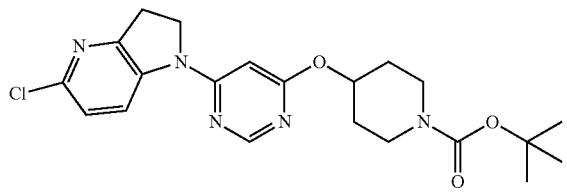

20-1

Step 20A: 5-Chloro-2,3-dihydro-1H-pyrrolo[3,2-b]pyridine (20a)

5-Chloro-1,3-dihydro-pyrrolo[3,2-b]pyridin-2-one (78 mg, 0.46 mmol) was dissolved in THF (1.5 mL). BH$_3$ (1M in THF, 0.92 mL, 0.92 mmol) was added and the mixture was stirred at 60° C. for 3 h. The mixture was cooled to room temperature, diluted with THF and quenched with 1N HCl. The mixture was treated with 2N NaOH until basic and was extracted with ether. The organic extracts were dried, filtered and evaporated to afford 20a.

Step 20B: 4-[6-(5-Chloro-2,3-dihydro-pyrrolo[3,2-b]pyridin-1-yl)-pyrimidin-4-yloxy]-piperidine-1-carboxylic acid tert-butyl ester (20-1)

20a (36 mg, 0.23 mmol) was dissolved in DMF (1.5 mL) with NaH (60% suspension, 9.6 mg, 0.24 mmol). 3a (75 mg, 0.24 mmol) was added slowly. The mixture was stirred at 90° C. for 8 h then cooled down to room temperature, diluted with ethyl acetate and washed with saturated NaHCO$_3$. The organic layer was isolated, dried, filtered and evaporated. The residue was purified by preparative HPLC to afford 20-1, LCMS 432.1 (MH+). $t_R$=5.21 (Method 5). EC50: 751 nM.

Example 21

4-[6-(5-Methanesulfonyl-2,3-dihydro-indol-1-yl)-pyrimidin-4-yloxy]-piperidine-1-carboxylic acid 1-(2-fluoro-benzyl)-pyrrolidin-3-yl ester

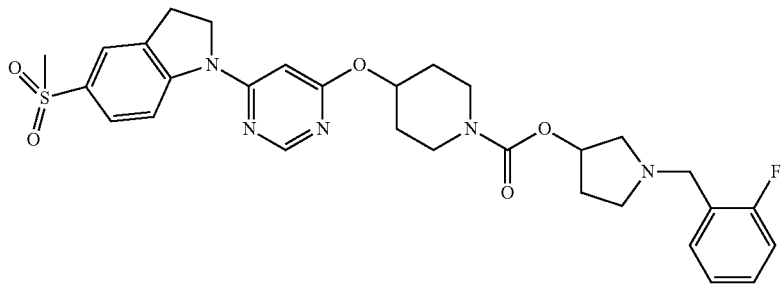

21-1

Step 21A: 4-[6-(5-Methanesulfonyl-2,3-dihydro-indol-1-yl)-pyrimidin-4-yloxy]-piperidine-1-carboxylic acid 1-tert-butoxycarbonyl-pyrrolidin-3-yl ester (21a)

3-Hydroxy-pyrrolidine-1-carboxylic acid tert-butyl ester (0.37 g, 2 mmol) was dissolved in 4 mL of DCM with triethylamine (0.28 mL, 2 mmol). 4-Nitro-benzoyl chloride (0.4 g, 2 mmol) was added and the mixture was stirred at room temperature for 12 h. It was then diluted with DCM and washed with saturated NaHCO$_3$ (3×20 mL). The organic layer was dried, filtered and evaporated. The residue was dissolved in DCM (4 mL) with triethylamine (0.36 mL, 2.6 mmol) and 4b (0.49 g, 1.3 mmol) was added. The mixture was stirred at room temperature for 8 h, diluted with DCM and washed with saturated NaHCO$_3$. The organic layer was evaporated to afford 21a, LCMS 588.2 (MH+).

Step 21B: 4-[6-(5-Methanesulfonyl-2,3-dihydro-indol-1-yl)-pyrimidin-4-yloxy]-piperidine-1-carboxylic acid pyrrolidin-3-yl ester (21b)

21a was dissolved in 2.5 mL of DCM and 2.5 mL of TFA was added. The mixture was stirred at room temperature for 2 h then evaporated and the crude material was dissolved in DCM, washed with saturated NaHCO$_3$ (3×10 mL), dried, filtered and evaporated to afford 21b.

Step 21C: 4-[6-(5-Methanesulfonyl-2,3-dihydro-indol-1-yl)-pyrimidin-4-yloxy]-piperidine-1-carboxylic acid 1-(2-fluoro-benzyl)-pyrrolidin-3-yl ester (21-1)

2-Fluoro-benzaldehyde (11 μL, 0.1 mmol) was dissolved in 1 mL of DCE with 21b (49 mg, 0.1 mmol) and NaBH(OAc)$_3$ (30 mg, 0.14 mmol). The mixture was stirred for 8 h at room temperature then was diluted with DCM and quenched with saturated NaHCO$_3$. The organic layer was washed with saturated NaHCO$_3$ followed by brine. The organic layer was dried, filtered and evaporated. The residue was purified by preparative HPLC to afford 21-1, LCMS 596.2 (MH+).

The following compounds were made according to this procedure using the corresponding aldehyde in the last step:

| No. | R | MH+ | MW | Retention Time (Min) | HPLC Gradient | EC50 (nM) |
|---|---|---|---|---|---|---|
| 21-1 | 2-fluorobenzyl | 596.2 | 595.7 | 4.92 | Method 2 | 78%* |
| 21-2 | 3-fluorobenzyl | 596.2 | 595.7 | 5.02 | Method 2 | 278 |
| 21-3 | 4-fluorobenzyl | 596.1 | 595.7 | 5.00 | Method 2 | 335 |
| 21-4 | 2,3-difluorobenzyl | 614.1 | 613.7 | 4.91 | Method 2 | 343 |
| 21-5 | 3,5-difluorobenzyl | 614.1 | 613.7 | 5.11 | Method 2 | 308 |
| 21-6 | 2,6-difluorobenzyl | 614.1 | 613.7 | 4.96 | Method 2 | 84%* |

*% values mean stimulation in % at 10 μM.

Example 22

4-[6-(5-Methanesulfonyl-2,3-dihydro-indol-1-yl)-pyrimidin-4-yloxy]-piperidine-1-carboxylic acid azetidin-3-yl ester

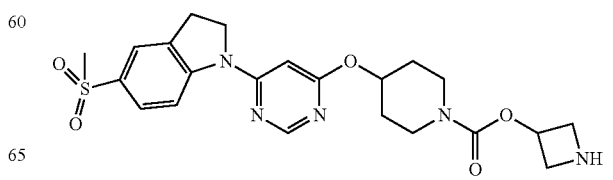

22-1

Step 22A: 4-[6-(5-Methanesulfonyl-2,3-dihydro-indol-1-yl)-pyrimidin-4-yloxy]-piperidine-1-carboxylic acid 1-tert-butoxycarbonyl-azetidin-3-yl ester (22a)

3-Hydroxy-azetidine-1-carboxylic acid tert-butyl ester (0.17 g, 1 mmol) was dissolved in 3 mL of DCM with triethylamine (0.28 mL, 2 mmol). 4-Nitro-benzoyl chloride (0.2 g, 1 mmol) was added and the mixture was stirred at room temperature for 12 h. A fifth of the solution was reacted with 4b (75 mg, 0.2 mmol). The mixture was stirred at room temperature for 8 h, diluted with DCM and washed with saturated NaHCO₃. The organic layer was evaporated to afford crude 22a, LCMS 574.2 (MH+).

Step 22B: 4-[6-(5-Methanesulfonyl-2,3-dihydro-indol-1-yl)-pyrimidin-4-yloxy]-piperidine-1-carboxylic acid azetidin-3-yl ester (22-1)

Half of 22a was dissolved in 2.5 mL of DCM and 2.5 mL of TFA was added. The mixture was stirred at room temperature for 2 h then evaporated. The crude material was purified by preparative HPLC to afford 22-1, LCMS 474.1 (MH+).

The following compounds were made according to this procedure using the corresponding starting material alcohol:

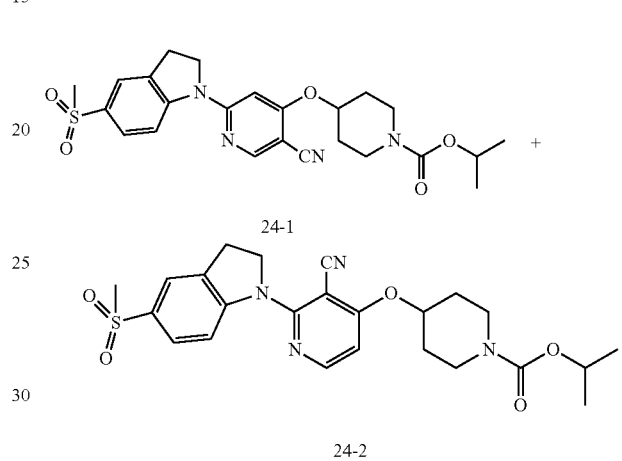

| No. | R⁶ | MH+ | MW | Retention Time (Min) | HPLC Gradient |
|---|---|---|---|---|---|
| 22-1 | azetidin-3-yl | 474.1 | 473.5 | 3.98 | Method 2 |
| 22-2 | piperidin-4-yl | 502.1 | 501.6 | 4.14 | Method 2 |

Example 23

4-[6-(5-Methanesulfonyl-2,3-dihydro-indol-1-yl)-pyrimidin-4-yloxy]-piperidine-1-carboxylic acid pyrrolidin-3-yl ester

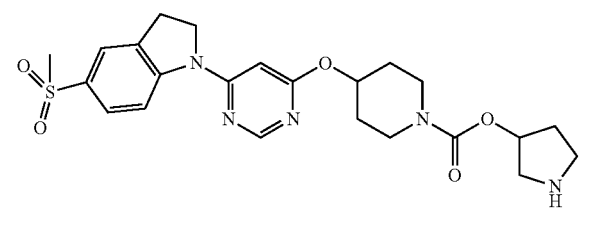

23-1

Step 23A: 4-[6-(5-Methanesulfonyl-2,3-dihydro-indol-1-yl)-pyrimidin-4-yloxy]-piperidine-1-carboxylic acid 1-benzyl-pyrrolidin-3-yl ester (23a)

23a (LCMS 578.2 (MH+)) was prepared according to step 22A using the corresponding starting material alcohol.

Step 23B: 4-[6-(5-Methanesulfonyl-2,3-dihydro-indol-1-yl)-pyrimidin-4-yloxy]-piperidine-1-carboxylic acid pyrrolidin-3-yl ester (23-1)

23a (0.2 mmol) and 30 mg of Pd/C in 3 mL of ethanol were stirred under 60 psi of hydrogen for 12 h. The suspension was filtered on celite with ethanol, evaporated and purified by preparative HPLC to afford 23-1, LCMS 488.1 (MH+). $t_R$=5.21 (Method 5).

Example 24

4-[5-Cyano-2-(5-methanesulfonyl-2,3-dihydro-indol-1-yl)-pyridin-4-yloxy]-piperidine-1-carboxylic acid isopropyl ester and 4-[3-Cyano-4-(5-methanesulfonyl-2,3-dihydro-indol-1-yl)-pyridin-2-yloxy]-piperidine-1-carboxylic acid isopropyl ester 24-1

24-2

Step 24A: 4-[5-Bromo-2-(5-methanesulfonyl-2,3-dihydro-indol-1-yl)-pyridin-4-yloxy]-piperidine-1-carboxylic acid isopropyl ester (24a) and 4-[3-Bromo-4-(5-methanesulfonyl-2,3-dihydro-indol-1-yl)-pyridin-2-yloxy]-piperidine-1-carboxylic acid isopropyl ester (24b)

To a solution of 10a (0.15 g, 0.5 mmol) in 2 mL of acetonitrile, was added bromine (0.1 mL, 1.95 mmol). The mixture was stirred at room temperature for 6 h then evaporated. The residue was added to a pre-stirred suspension of NaH (60% in oil, 9 mg, 0.22 mmol) and 5-methanesulfonyl-2,3-dihydro-1H-indole (43 mg, 0.22 mmol) in 1 mL of DMF. The mixture was stirred at 90° C. for 12 h, quenched with water, extracted with ethyl acetate and evaporated. The residue was purified by silica gel chromatography (eluent: 20% ethyl acetate in hexane) to afford 24a and 24b (80 mg of the less polar product and 55 mg of the more polar product).

Step 24B: 4-[5-Cyano-2-(5-methanesulfonyl-2,3-dihydro-indol-1-yl)-pyridin-4-yloxy]-piperidine-1-carboxylic acid isopropyl ester (24-1) and 4-[3-Cyano-4-(5-methanesulfonyl-2,3-dihydro-indol-1-yl)-pyridin-2-yloxy]-piperidine-1-carboxylic acid isopropyl ester (24-2)

24a (50 mg, 0.09 mmol) was dissolved in DMF (0.5 mL) with CuCN (9 mg, 0.1 mmol) and heated at 90° C. for 8 h. CuCN (18 mg, 0.2 mmol) was added and the heating was continued for an additional 40 h. The mixture was diluted with ethyl acetate and washed with water, saturated NaHCO₃ and brine. The organic layer was isolated, dried, filtered and evaporated. The residue was purified by preparative HPLC to afford 24-1, LCMS 485.1 (MH+). 54% stimulation at 10 μM.

4-[3-Cyano-4-(5-methanesulfonyl-2,3-dihydro-indol-1-yl)-pyridin-2-yloxy]-piperidine-1-carboxylic acid isopropyl ester (24-2) was obtained similarly.

Example 25

In Vivo OGTT Methods

Nine to 13 week old Male Sprague Dawley rats weighing 250 g-350 g or 9 week old male Zucker Diabetic Fatty rats weighing 300 g-450 g were fasted overnight for 16 hours. At time zero, blood was collected using the tail-nick method and glucose was measured with a glucometer (Bayer Health-Care). Animals then immediately received either vehicle (80% Labrasol, Gattefossé, France) or 3, 10, or 30 mg/kg a GPR119 agonist according to this invention (p.o., volume 2 mL/kg). Thirty minutes later blood glucose was again measured preceding the administration of a glucose bolus (p.o. 2 g/kg, volume 6 mL/kg)). Blood glucose was then determined at 10, 20, 30, 60, 90, 120, and 180 minutes post glucose bolus.

Example 26 cAMP Assay Methods

Quantitative detection of cAMP accumulation from cells expressing human GPR119 receptor was achieved using Perkin Elmer's LANCE cAMP-384 Kit (Cat#AD0264) according to the manufacturer's protocol. Briefly, HEK293 cells stably expressing a mutant form of the human GPR119 receptor (Methionine 1 replaced with the amino acid sequence MKTIIALSYIFCLVFADYKDDDDA, and T327 & S329 changed to alanines) were grown to 50-70% confluency in cell culture media (DMEM, 10% heat inactivated Fetal Bovine Serum, 50 I.U./mL penicillin, 50 μg/mL streptomycin, 10 mM HEPES, 20 μg/mL G418 Sulfate). On the day of the assay, GPR119 stable HEK293 cells were lifted from the tissue culture plate and 1000 cells/well were incubated along with various concentrations of test compounds for 20 min at 37° C. Detection Buffer (50 mM HEPES, 10 mM calcium chloride, 0.35% Triton X-100, 1 mg/mL BSA) containing cAMP-specific antibody was then added to all wells and allowed to equilibrate in the dark for 10 minutes at room temperature. Upon equilibration, Detection Buffer containing europium-labeled cAMP tracer complex was added to all wells and allowed to react for 1 hour at room temperature. After 1 hour, bound europium-labeled cAMP tracer was measured using a Perkin Elmer ViewLux. The quantity of cAMP generated in each well was derived from a standard curve.

For some compounds for which no EC50 value could be determined, the efficacy is provided at a single concentration (10 μM) yielding % stimulation values.

Example 27

Insulin Secretion Assay in Isolated Rat Pancreatic Islets

Rat pancreatic islets are isolated and allowed to recover overnight in RPMI cell culture media (10% FBS, 50 I.U./mL penicillin, 50 μg/mL streptomycin, 10 mM HEPES) containing 11 mM Glucose. After incubating overnight at 37° C. and 5% $CO_2$/95% air, the islets were thoroughly washed 5× in 1× Krebes Ringes HEPES buffer (118 mM NaCl, 4.8 mM KCl, 2.5 mM $CaCl_2$, 1.2 mM $MgSO_4$, 20 mM HEPES, 0.1% BSA, adjusted to a pH of 7.4 with NaOH) with 5 mM Glucose. Islets were allowed to preincubate for 30 minutes in 1×KRH with 5 mM Glucose at 37° C. before assay initiation.

Test compounds are diluted in 1×KRH containing an appropriate concentration of glucose so that at the initiation of the islet assay the final glucose concentration was 8.3 mM. At time zero, compound solutions were added to islets in wells to give a final volume of 2.4 mL of 1×KRH with 8.3 mM glucose and allowed to incubate at 37° C. Aliquots of supernatant were removed at various times points and were assayed for insulin using a commercially available insulin RIA kit (Linco Research Labs).

Immediately following the assay, the islets are removed from the 24 well plates into separate 1.5 mL epindorf tubes containing 1 mL of 1×KRH with no glucose and then placed on ice. Islets are allowed to settle for 5 min before the supernatant is removed and 300 μL of acid/ethanol is added to each tubes. Following brief sonication tubes are stored at −20° C. for at least 24 hours before assayed for total insulin content. For quantification purposes, the amount of stimulated insulin secretion is expressed as a fraction of total insulin in the assay well.

It will be appreciated that, although specific embodiments of the invention have been described herein for purposes of illustration, various modifications may be made without departing from the spirit and scope of the invention. Accordingly, the invention is not limited except as by the appended claims.

What is claimed is:

1. A compound of the formula (I):

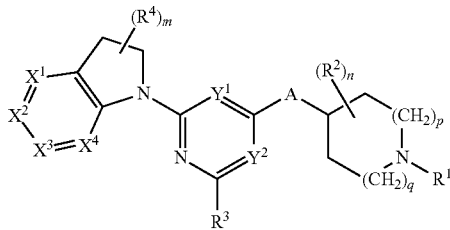

wherein:
$X^1$, $X^2$, $X^3$, and $X^4$ are independently —N— or —C($R^5$)—;
$Y^1$ is —N— and $Y^2$ —C($R^3$)—, or $Y^1$ is —C($R^3$)— and $Y^2$ is —N—;
A is —N($R^7$)—;
$R^1$ is $R^{Alk}$, aryl-$C_{1-4}$alkyl, heterocycle-$C_{1-4}$alkyl, —C(=O)$R^7$, —CO$_2R^6$, —SO$_2R^6$, —C(=O)N($R^7$)$_2$, —C(=S)N($R^7$)$_2$, aryl, or heterocycle, wherein each $R^{Alk}$, alkyl, aryl and heterocycle are optionally substituted with 1-4 substituents independently of each other selected from $R^9$;
$R^2$ at each occurrence is independently $C_{1-4}$alkyl, F, hydroxy, or $C_{1-4}$alky-O—;
$R^3$ at each occurrence is independently H, halogen, CN, $C_{1-4}$alkyl, $C_{1-4}$alkyl-O— or $C_{1-4}$alkyl-S—;
$R^4$ at each occurrence is independently H, halogen, or $C_{1-4}$alkyl;
$R^5$ at each occurrence is independently H, halogen, cyano, hydroxy, $R^{Alk}$, halo$C_{1-4}$alkyl, —NO$_2$, —C(=O)$R^6$, —CO$_2R^6$, —C(=O)N($R^7$)$_2$, —SO$_2$N($R^7$)$_2$, —S(=O) $R^6$, —S(=O)$_2R^6$, $C_{1-6}$alkyl-O—, halo$C_{1-6}$alkyl-O—, —N($R^7$)$_2$, $C_{1-6}$alkyl-S—, aryl, aryl-$C_{1-6}$alkyl, heterocycle, heterocycle-$C_{1-6}$alkyl, —NR$^7$C(=O)$R^6$, —NR$^7$C(=O)N($R^7$)$_2$, —NR$^7$C(=O)OR$^7$, —NR$^7$C(=NR$^7$)N($R^7$)$_2$, or —NR$^7$S(=O)$_2$N($R^7$)$_2$ wherein each $R^{Alk}$, alkyl, aryl, and heterocycle are optionally substituted with 1-5 substituents independently of each other selected from $R^9$;
$R^6$ is $R^{Alk}$, heterocycle, heterocycle-$C_{1-3}$-alkyl, or aryl, wherein each $R^{Alk}$, alkyl, heterocycle and aryl is optionally substituted with 1-4 substituents independently of each other selected from $R^9$;
$R^7$ at each occurrence is independently H or $R^{Alk}$ wherein each $R^{Alk}$ is optionally substituted with 1-4 substituents independently of each other selected from halogen, hydroxy, —N($R^8$)$_2$, $C_{1-4}$alkyl-O—, and —CO$_2R^8$;
$R^8$ at each occurrence is independently H or $C_{1-4}$alkyl;
$R^9$ is at each occurrence is independently cyano, hydroxy, $R^{Alk}$, aryl, aryl-$C_{1-3}$-alkyl, heterocycle, halogen, oxo, $C_{1-4}$haloalkyl, —NO$_2$, —C(=O)H, —CO$_2R^8$, —OC(=O)$R^{Alk}$, —C(=O)N($R^7$)$_2$, —SO$_2$N($R^7$)$_2$, —S(=O) $R^{Alk}$, —S(=O)$_2R^{Alk}$, $C_{1-6}$alkoxy, halo$C_{1-4}$alkoxy, —N($R^7$)$_2$, —SR$^7$, —NR$^7$C(=O)$R^{Alk}$, —NR$^7$C(=O)OR$^{Alk}$ or —NR$^7$C(=O)N($R^7$)$_2$, wherein each $R^{Alk}$, alkyl, aryl and heterocycle are optionally substituted with 1-4 substituents independently of each other selected from halogen, hydroxy, —N($R^8$)$_2$, $C_{1-4}$alkyl-O—, —NR$^7$CO$_2R^7$, —NR$^7$SO$_2R^7$, and —CO$_2R^8$;
$R^{Alk}$ at each occurrence is independently $C_{1-6}$-alkyl, $C_{2-6}$-alkenyl, $C_{2-6}$-alkynyl, $C_{3-8}$-cycloalkyl, $C_{3-8}$-cycloalkyl-$C_{1-3}$-alkyl, $C_{4-8}$-cycloalkenyl or $C_{4-8}$-cycloalkenyl-$C_{1-3}$-alkyl;
m is 0,1, or 2;
n is 0,1, or 2;
p is 0 or 1; and
q is 0,1, or 2,
a tautomer or stereoisomer thereof, or a salt thereof.

2. The compound according to claim 1 wherein $R^1$ is $C_{1-6}$alkyl, aryl-$C_{1-4}$alkyl, heterocycle-$C_{1-4}$alkyl, aryl, or heterocycle, wherein each alkyl, aryl and heterocycle are optionally substituted with 1-4 substituents independently of each other selected from $R^9$, or a salt thereof.

3. The compound according to claim 1 wherein $R^1$ is —C(=O)$R^7$, —CO$_2R^6$, or —C(=O)N($R^7$)$_2$, or a salt thereof.

4. The compound according to claim 3 wherein $R^1$ is —CO$_2R^6$, or a salt thereof.

5. The compound according to claim 4 wherein $R^6$ is $C_{1-6}$alkyl, or a salt thereof.

6. The compound according to claim 1 wherein n is 0, or a salt thereof.

7. The compound according to claim 1 wherein p and q are 1, or a salt thereof.

8. A pharmaceutically acceptable salt of the compound according to claim 1.

9. A pharmaceutical composition comprising the compound of claim 1, or a pharmaceutically acceptable salt thereof, and one or more pharmaceutically acceptable carriers and/or diluents.

10. A method for treating type-2 diabetes or obesity in a patient in need thereof characterized in that a compound according to claim 1, or a pharmaceutically acceptable salt thereof, is administered to the patient.

11. A method for treating type-2 diabetes or obesity in a patient in need thereof comprising the step of administering to the patient a therapeutically effective amount of a compound according to claim 1, or a pharmaceutically acceptable salt thereof, in combination with a therapeutically effective amount of one or more additional therapeutic agents.

12. A pharmaceutical composition comprising a compound according to claim 1, or a pharmaceutically acceptable salt thereof, and one or more additional therapeutic agents, optionally together with one or more pharmaceutically acceptable carriers and/or diluents.

13. The compound according to claim 1 of the formula (I6):

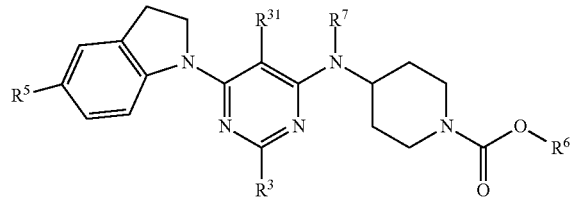

wherein:
$R^3$ and $R^{31}$ are each H;
$R^5$ is halogen, —NO$_2$ or —S(=O)$_2$—$C_{1-4}$-alkyl;
$R^6$ is $C_{1-4}$-alkyl, $C_{3-6}$-cycloalkyl or $C_{3-6}$-cycloalkyl-$C_{1-3}$-alkyl, wherein each of the beforementioned groups is optionally substituted with 1 to 4 substituents independently of each other selected from F and $C_{1-3}$-alkyl-O—; and
$R^7$ is H, $C_{1-4}$-alkyl, $C_{3-4}$-alkenyl or $C_{1-3}$-alkyl-O—$C_{1-3}$-alkyl,
a tautomer or stereoisomer thereof, or a salt thereof.

14. The compound according to claim 13, wherein $R^5$ is F, Cl, —NO$_2$ or —S(=O)$_2$—CH$_3$; and $R^6$ is i-propyl, sec-butyl, tert-butyl, cyclopropyl or cyclopropyl-methyl-, all of which are optionally substituted with one or more F or $C_{1-3}$-alkyl-O—.

15. The compound according to claim 1 selected from:

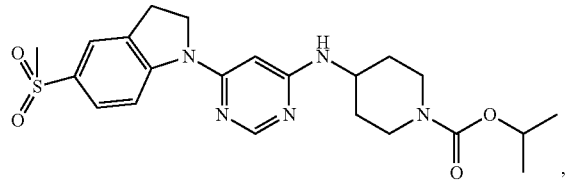

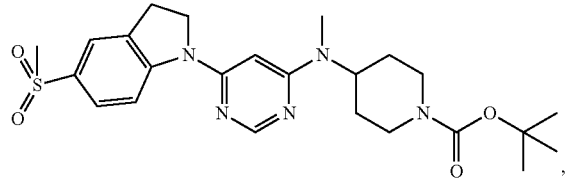

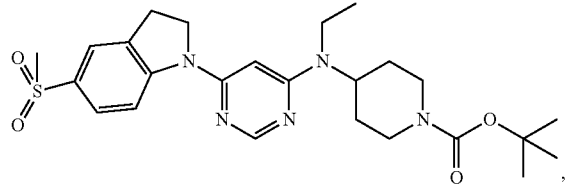

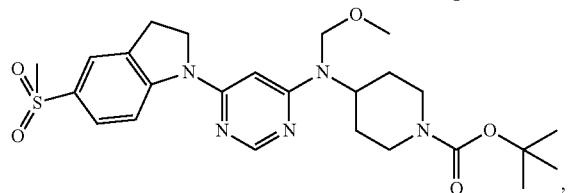

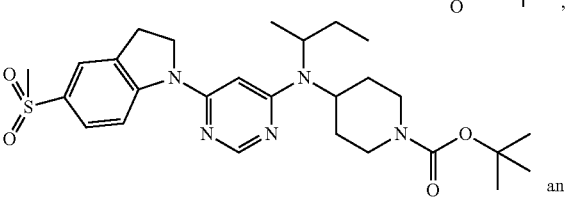
and

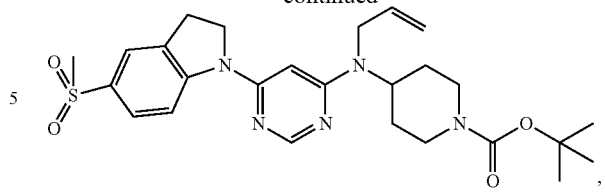

or a salt thereof.

16. A pharmaceutical composition comprising the compound of claim 13, or a pharmaceutically acceptable salt thereof, and one or more pharmaceutically acceptable carriers and/or diluents.

17. A pharmaceutical composition comprising a compound according to claim 13, or a pharmaceutically acceptable salt thereof, and one or more additional therapeutic agents, optionally together with one or more pharmaceutically acceptable carriers and/or diluents.

18. A method for treating type-2 diabetes or obesity, characterized in that a compound according to claim 13, or a pharmaceutically acceptable salt thereof, is administered to a patient in need thereof.

19. The method of claim 18, wherein the method is for treating type-2 diabetes.

20. A method for treating type-2 diabetes or obesity, comprising the step of administering to the patient a therapeutically effective amount of a compound according to claim 13, or a pharmaceutically acceptable salt thereof, in combination with a therapeutically effective amount of one or more additional therapeutic agents to a patient in need thereof.

21. The method of claim 20, wherein the method is for treating type-2 diabetes.

22. A pharmaceutically acceptable salt of the compound according to claim 13.

* * * * *

```
                        SEQUENCE LISTING

<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Lys Thr Ile Ile Ala Leu Ser Tyr Ile Phe Cys Leu Val Phe Ala
1               5                   10                  15

Asp Tyr Lys Asp Asp Asp Asp Ala
            20
```